US005690103A

United States Patent [19]
Groth et al.

[11] Patent Number: 5,690,103
[45] Date of Patent: Nov. 25, 1997

[54] DETECTION/EXCLUSION OF ACUTE MYOCARDIAL INFARCTION USING NEURAL NETWORK ANALYSIS OF MEASUREMENTS OF BIOCHEMICAL MARKERS

[76] Inventors: Torgny Lars Groth, Döbelnsgatan 24A, S-752 37 Uppsala; Johan Ellenius, Geijersgatan 15B, S-752 26 Uppsala, both of Sweden

[21] Appl. No.: 668,260

[22] Filed: Jun. 20, 1996

[51] Int. Cl.$^6$ ............................................. A61B 5/14
[52] U.S. Cl. ................................. 128/632; 128/924
[58] Field of Search ............................. 128/632, 924

[56] References Cited

PUBLICATIONS

"Emergency Department: Rapid Identification and Treatment of Patients With Acute Myocardial Infarction" National Heart Attack Alert Program Coordinating Committee, 60 Minutes To Treatment Working Group, Bethesda, Maryland, Annals of Emergency Medicine, Feb. 1994, pp. 311–329.

"Early Diagnosis and exclusion of acute myocardial infarction using biochemical monitoring", Bertil Lindahl, et al., Coronary Artery Disease 1995, vol. 6, No. 4, pp. 321–328 Uppsala, Sweden.

"Neural Network Analysis of Serial Cardiac Enzyme Data" James W. Furlong et al., Am J Clin Pathol 1991; 96, No. 1, pp. 134–141.

"Using data preprocessing and single layer perceptron to analyze laboratory data", J. J. Forsstrom et al, Turku, Finland, Scand J Clin Lab Invest 1995; 55, Suppl. 222, pp. 75–81.

"Use of neural networks to diagnose acute myocardial infarction". I. Methodology, Jorgen S. Jorgensen, Denmark, Clinical Chemistry 42: 4 1996, pp. 604–612.

"Use of neural networks to diagnose acute myocardial infarction, II. A clinical application", Susanne M. Perdersen, Denmark, Clinical chemistry 42:4, 1996, pp. 613–617.

"More Rapid biochemical Diagnosis of Myocardial Infarction: Necessary? Prudent? Cost Effective?" Department of Medicine, St. Louis, Missouri, Clinical Chemistry, vol. 39, No. 8, 1993 pp. 1567–1569.

"Biochemical Markers in Suspected Acute Myocardial Infarction: The Need for Early Assessment", L. Kristin Newby et al., Duke University Medical Center, Durham, NC, Clinical Chemistry, vol. 41, No. 9, 1995, pp. 1263–1265.

"Neural Networks and Related Methods for Classification" B. D. Ripley, United Kingdom, J.R. Statist, Soc. B, 56, No. 3, 1994, pp. 409–456.

"Finding Structure in Time", Jeffrey L. Elman, California, Cognitive Science 14, 1990, pp. 179–211.

"Introduction To The Theory Of Neural Computation", Hertz, Krogh and Palmer, Lecture notes vol. I, Addison–Wesley Publishing Company, 1991, pp. 141–144.

"Randomised Trial Of Intravenous Streptokinase, Oral, Aspirin, Both, Or Neither Among 17 187 Cases Of Suspected Acute Myocardial Infarction:" ISIS–2 (Second International Study Of Infarct Survival) Collaborative Group, The Lancet Ltd. I, 1988, UK, pp. 349–360.

(List continued on next page.)

*Primary Examiner*—William E. Kamm
*Attorney, Agent, or Firm*—Young & Thompson

[57] ABSTRACT

The overall invention categorizes patients with suspected acute myocardial infarction (AMI) with regard to a) AMI/non-AMI; b) infarct size (e.g. Major/Minor); c) time since onset of infarction; and d) non-AMI with/without minor myocardial damage (MMD). Generally, the above categorization is based on frequent timed blood sampling and measurement of selected biochemical markers of AMI with different rates of appearance in circulating blood. The computations are performed by using specially designed artificial neural networks. According to a first main aspect of the invention, early, i.e. generally within 3 hours from admission of the patient, detection/exclusion of acute myocardial infarction is provided. Furthermore, early prediction of the infarct size and early estimation of the time from onset are also provided.

35 Claims, 18 Drawing Sheets

PUBLICATIONS

"A Comparison Of Immediate Angioplasty With Thrombolytic Therapy For Acute Myocardial Infarction", Cindy L. Grines, M.D., et al. The New England Journal of Medicine, vol. 328, No. 10, 1993, Massachusettes Medical Society, pp. 673–679.

"Indications for fibrinolytic therapy in suspected acute myocardial infarction: collaborative overview of early mortality and major morbidity results from all randomised trial of more than 1000 patients", Fibrinolytic Therapy Trialists' (FTT) Collaborative Group, UK, The Lancet, vol. 343, 1994, pp. 311–322.

"Prognostic Significance of the Extent of Myocardial Injury in Acute Myocardial Infarction Treated by Streptokinase (the GISSI Trial)", Francesco Mauri, MD, et al., Italy, The American Journal of Cardiology, vol. 63, No. 18, 1989, pp. 1291–1295.

DETECTION/EXCLUSION OF ACUTE MYOCARDIAL INFARCTION USING NEURAL NETWORK ANALYSIS OF MEASUREMENTS OF BIOCHEMICAL MARKERS

TECHNICAL FIELD OF THE INVENTION

The present invention relates to the management of patients with suspected myocardial infarction or damage, and more particularly to methods and apparatuses for early detection/exclusion of AMI, early prediction of infarct size, estimation of time from onset of infarction, and assessment of minor myocardial damage.

BACKGROUND OF INVENTION

An early diagnosis within the first hours after onset of symptoms is essential for the optimal treatment of patients with acute myocardial infarction (AMI) as has been documented by e.g. the National Heart Attack Alert Program Coordinating Committee, 60 minutes to Treatment Working Group (in Ann Emerg Med 1994; 23:311–329). In patients with ST-elevation in their initial ECG recording on admission the diagnosis is straight forward. Moreover, the total sum of ST-elevations in all ECG-leads gives a good estimate of the myocardium at risk. However, in at least 40% of patients with AMI the 12-lead ECG is nondiagnostic on admission. In these patients the diagnosis has to be based on clinical data and measurements of biochemical markers, currently a time consuming procedure that causes delay in start of treatment. An early and reliable prediction of the infarct size is also difficult for this group of patients. In the heterogeneous group of patients admitted to the hospital because of chest pain, considerable economic gains might be achieved by early identification of those patients (approximately 60–70%) who are at sufficiently low risk of AMI and its complications, to be transferred to a general ward outside the coronary care unit (CCU). Among patients with unstable angina 30–50% have minor elevations of sensitive biochemical markers such as creatine kinase MB and troponin-T. The term minor myocardial damage (MMD) has been proposed for these minor elevations. Since MMD indicates an increased risk of future cardiac events it seems important not only to detect AMI, but also to detect MMD as early as possible.

Thus, in the early management of patients with acute chest pain there are several important diagnostic issues to be addressed. Does the patient have AMI? If so will the ultimate infarct size be large or small? What is the timing of the infarction? If the patient does not have an AMI: Does the patient have a high or low risk for subsequent cardiac events? The clinician has to consider the patient's history and physical status, the results of ECG and blood tests etc. This decision-making process may be time consuming and is heavily dependent on the clinician's knowledge and experience.

Several different methods have been proposed to support these decisions, e.g. the use of diagnostic algorithms based on clinical data, and measurements of new biochemical markers of myocardial damage. In the study by Lindahl et al. in Coronary Artery Disease 1995; 6:321–328 early detection and exclusion of AMI was performed with the use of myoglobin, creatine kinase MB and troponin-T, and simple empirical rules. Computer methods using artificial neural networks have been applied for AMI diagnosis based on clinical data and biochemical markers:

The study by Furlong et at., reported in Am J Clin Pathol 1991; 96:134–141, was based on a panel often enzymes: CK, CK-MM, CK-MB, CK-BB, LDH, LDH-1–5, with measurements at two different time points 48 hours or less apart. Representative examples in Furlong's article clearly indicates that the time interval between the two measurements is so large (e.g. $\Delta t=7.4$; 23.7; 36.5 hours) that the method is obviously not intended to be used in a clinical application for early detection of AMI.

An illustration by Forsström et al. in Scand J Clin Lab Invest 1995;55(suppl 222):75–81, was based on "measurements of creatine kinase at admission, after 6 hours and after 12 hours from admission, and lactate dehydrogenase after 6 hours and 12 hours from admission". However, an evaluation of the measurement results can not be made until the last measurement at 12 hours from admission has been made.

In a recent paper (Clin Chem 1996;42(4):604–612; and 613–617) Jörgensen et al. investigated the diagnostic performance of neural networks trained on various combinations of ECG data, and serum concentrations of CKB, LD1 and potassium, on admission, 12 and 24 hours after admission.

In short, the neural network applications by Furlong et al., Forsström et al., and Jörgensen et al. have not addressed the problem of early diagnosis of AMI.

Furthermore, it is important to understand that several hours after admission, the patterns of the marker concentrations are generally so pronounced that the clinicians themselves can easily assess AMI therefrom without using neural network support. Besides, 12 hours after admission, the potential benefit of thrombolytic treatment has decreased to a very low level.

Biochemical markers have been used for many years in the late diagnosis/exclusion of AMI and for infarct size estimation. During recent years the interest has been focused on 'more rapid biochemical diagnosis of myocardial infarction' as discussed in an editorial in Clin Chem 1993; 39/8:1561567–1569

There are important differences in the properties of the markers of today, e.g. myoglobin, CK-MB and cardiac troponin-T. An increase of myoglobin mass concentration can be measured in plasma already after 1–2 hours after the infarct onset, while CK-MB and troponin-T starts to increase after 3–4 hours. Troponin-T remains elevated up to three weeks after an AMI, while CK-MB remains elevated for 2–3 days and myoglobin for one day. For all three markers the diagnostic sensitivity for AMI is high. A minor elevation of troponin-T and CK-MB, indicating minor myocardial damage, can be detected in at least 30% of all patients with the diagnosis of unstable angina according to conventional criteria. Myoglobin has a poor diagnostic specificity since myoglobin is also released from damaged skeletal muscles.

SUMMARY OF THE INVENTION

Early detection/exclusion is essential for the handling and management of patients with suspected acute myocardial infarction (AMI). For many patients, the ECG is nondiagnostic on admission and other methods based on clinical and/or biochemical data have to be used. However, the clinical application of early biochemical markers will require further development, as concluded by Newby et al. in an editorial in Clin Chem 1995;41(9):1263–1265.

A main object of the present invention is to improve the management, and more particularly the early management, of patients with suspected myocardial infarction or damage, based on measurements of biochemical markers of AMI.

An important object of the invention is to provide methods and apparatuses for early, i.e. generally within 3 hours from admission of the patient or within 3-6 hours from onset of infarction, detection/exclusion of acute myocardial infarction.

Furthermore, another important object of the invention is to make an early prediction of the infarct size. An early infarct size prediction is of crucial importance since the potential benefit of thrombolytic treatment of the patient is related to the infarct size.

Yet another object of the invention is to make an estimate of the timing of the infarction, and by that provide a 'second opinion' to the patient's own subjective estimate of the time since onset of symptoms of infarction.

If acute myocardial infarction has been excluded it is a further object of the invention to make an assessment of whether the patient has a high or low risk for future cardiac events.

Still another important object of the invention is to provide methods and apparatuses which integrate two or more of the following technical features:

detection/exclusion of acute myocardial infarction;
prediction of the infarct size;
estimation of the timing of the infarction; and
assessment/exclusion of minor myocardial damage.

A series of embodiments of a method for detecting acute myocardial infarction according to the present invention are defined by the scope of the appended independent claims 1, 19, 21 and 32.

Different preferred embodiments of the method according to the independent claims 1, 19, 21 and 32 are defined by the corresponding dependent claims.

The embodiment according to claim 32 in particular is directed towards detection of AMI using inventive neural network training.

A method for:
a) early detection/exclusion of acute myocardial infarction (AMI) in a patient;
b) predicting the infarct size;
c) estimating the time after onset of infarction; and
d) assessing/excluding possible minor myocardial damage, is defined by the scope of the independent claim 20.

A series of embodiments of an apparatus for detecting acute myocardial infarction according to the invention are defined by the scope of the independent claims 12, 28, 30 and 31.

Different preferred embodiments of the apparatus according to the independent claims 12, 28, 30 and 31 are defined by the corresponding dependent claims.

The apparatus according to the independent claims 28, 30 and 31 in particular utilize neural network methodology in an inventive manner.

Furthermore, a method for excluding acute myocardial infarction according to the invention is defined by the scope of the independent claim 25.

An apparatus for excluding acute myocardial infarction according to the invention is defined by the scope of the independent claim 22.

In addition, the present invention provides a method for predicting the infarct size for a patient with acute myocardial infarction according to the independent claim 33.

The present invention also provides a method for assessing/excluding minor myocardial damage according to the independent claim 34.

Furthermore, the present invention provides a method for estimating the time since onset of infarction according to the independent claim 35.

The advantages afforded by the present invention will be appreciated upon reading of the below description of the embodiments of the invention.

BRIEF DESCRIPTION OF THE DRAWINGS

The novel features believed characteristic of the invention are set forth in the appended claims. The invention itself, however, as well as other features and advantages thereof will be best understood by reference to the detailed description of the specific embodiments which follows, when read in conjunction with the accompanying drawings, in which:

DETAILED DESCRIPTION OF EMBODIMENTS

The overall invention categorizes patients with suspected acute myocardial infarction (AMI) with regard to:

AMI/non-AMI;
infarct size (e.g. Major/Minor);
time since onset of infarction;
non-AMI with/without minor myocardial damage (MMD).

Generally, the above categorization is based on frequent timed blood sampling and measurement of selected markers of AMI with different rates of appearance in circulating blood. The computations are performed with use of specially designed artificial neural networks, hereinafter referred to as 'neural networks'. A neural network is regarded as a kind of computational structure which is trained on a representative set of preclassified example cases before it is applied for classification of unknown cases. Additional background on neural network classification can be obtained by reviewing 'Neural networks and related methods for classification' by Ripley B. D. in J R Statist Soc B 1994;56(3):409–456.

Parts of the overall invention are extracted into separate methods and apparatuses according to different aspects of the invention, all as will be described below.

First, however, the main principles of the overall invention are described in connection with FIG. 1.

Figure 1:
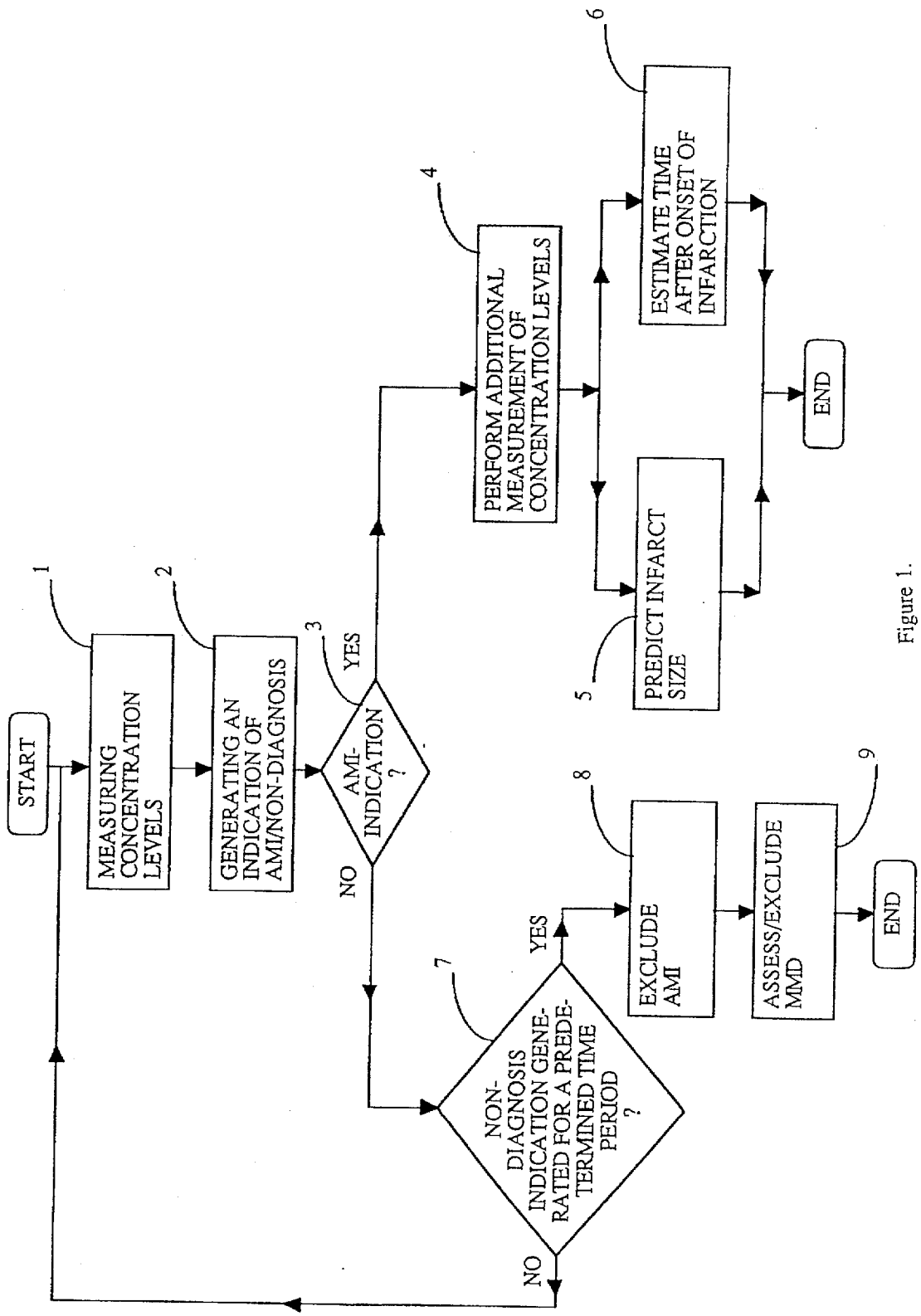
FIG. 1 is a schematic flow diagram illustrating the overall method according to an embodiment of the present invention.

FIG. 1 is a schematic flow diagram illustrating the overall method according to an embodiment of the present invention. In step 1, concentration levels of at least two biochemical markers of AMI in plasma of a patient are measured. Preferably, the first measurement of concentration levels is performed on admission of the patient. It should be understood that hereinafter the expression measurement of concentrations of biochemical markers generally means the whole process of taking blood samples and analyzing the samples to determine the concentration levels of the biochemical AMI-markers. Examples of biochemical AMI-markers are myoglobin, creatine kinase and cardiac troponins-I and T. The biochemical markers used according to the invention are selected such that they have different rates of appearance in plasma at AMI. In step 2 an indication of AMI/non-diagnosis is generated by making a comparison based on the measured concentration levels and first empirical data comprising concentration levels obtained from previous patients with AMI/non-AMI and a pre-classification of the presence/absence of AMI in these previous patients. More precisely, in step 2 it is generated either an indication of AMI or an indication of non-diagnosis. The non-diagnosis indication is also designated [?].

Step 3 is a simple test of whether an AMI-indication has been generated or not. If an indication of AMI has been generated (YES) then an additional measurement of the concentration levels is performed in step 4 and a prediction of the infarct size follows in step 5 and also an estimation of the time after onset of infarction in step 6.

If no indication of AMI has been generated (NO) then a test (step 7) is performed to check if the non-diagnosis indication has been generated for a predetermined period of time, e.g. 3 hours from the initial measurement.

If NO in step 7, the method starts over again at step 1 with a further measurement of the concentration levels. Now, step 2 is executed using these new concentration levels, or alternatively an accumulative set of concentration levels comprising the initial concentration levels and the concentration levels obtained from the further measurement, and so on. In general, a first predetermined set of all the concentration levels measured during the entire overall measuring process (including step 1 and step 4) is used for generating the indication of AMI/non-diagnosis in step 2. The overall measuring process is executed with a predetermined timing and generally within 3 hours from admission of the patient.

If YES in step 7, then AMI is excluded (step 8) and possible minor myocardial damage in the patient is assessed/excluded in step 9.

The prediction of the infarct size in step 5 is performed by making a comparison based on a second predetermined set of all of the concentration levels obtained during the entire measuring process and second empirical data comprising concentration levels obtained from previous patients with different infarct sizes and a pre-classification of the infarct sizes of these previous patients. Preferably, the second predetermined set comprises the concentration levels obtained from the last measurement of step 1 and the concentration levels measured in step 4.

The generation of an estimate representing a time period within which onset of infarction occurred, in step 6, is performed by making a comparison based on a third predetermined set of all the concentration levels obtained during the entire measuring process and third empirical data comprising concentration levels obtained from previous patients of different states regarding the time after onset of infarction and a preclassification of the times after onset for the previous patients. Generally, the second and third predetermined sets of concentration levels are identical.

In general, AMI is excluded if no AMI-indication has been generated and the indication of non-diagnosis has been generated for a predetermined period of time (see step 3, 7, 8). Provided AMI has been excluded, minor myocardial damage (MMD) is assessed/excluded by making a comparison based on a fourth predetermined set of all the concentration levels obtained during the entire measuring process and fourth empirical data comprising concentration levels obtained from previous patients with MMD/without MMD and a preclassification of the presence/absence of MMD in the previous patients (step 9).

Preferably, the fourth predetermined set comprises all of the concentration levels measured during the entire measuring process.

Preferably, all comparison procedures are performed using neural network methodology, details of which will be described below.

Normally, the measurements are performed with equidistant time intervals, such as every 15 or 30 minutes, but in general the exact setting of the predetermined measurement timing is not of crucial importance. Preferably, however, the predetermined timing generally corresponds to the timing with which the concentration levels of the empirical data were measured or obtained.

Using three biochemical markers of different appearance rates is believed to give the best trade-off between implementational complexity and the time required to generate a reliable indication of acute myocardial infarction. Preferably, biochemical markers of significantly different appearance rates are used, since marker-patterns of AM/normally protrude in a more distinct manner when these rates clearly differ from each other.

In an alternative embodiment, step 4 is not necessary for predicting the infarct size and estimating the timing of the infarction. If measurements of concentration levels have been executed at two or more time instances in step 1, then it is possible to use the concentration levels obtained in the two last measurements to predict the infarct size, and to estimate the time after onset of infarction.

As will be apparent from the more detailed description given below, the results show that it is possible to generate an AMI-indication for a patient with AMI based on the initially measured concentration levels of the biochemical markers. In this case, the first predetermined set comprises the concentration levels obtained from the initial measurement. If, for individual patients with AMI, it is not possible to generate an AMI-indication based on the initial measurement of the markers, then additional measurements are performed until AMI is detected.

In the flow diagram of FIG. 1 two separate trails are apparent. The first trail is concerned with detection of AMI, infarct size prediction and time estimation, while the other trail regards exclusion of AMI and assessment/exclusion of MMD. These trails mutually exclude each other, but still relate to the same invention.

Figure 2:
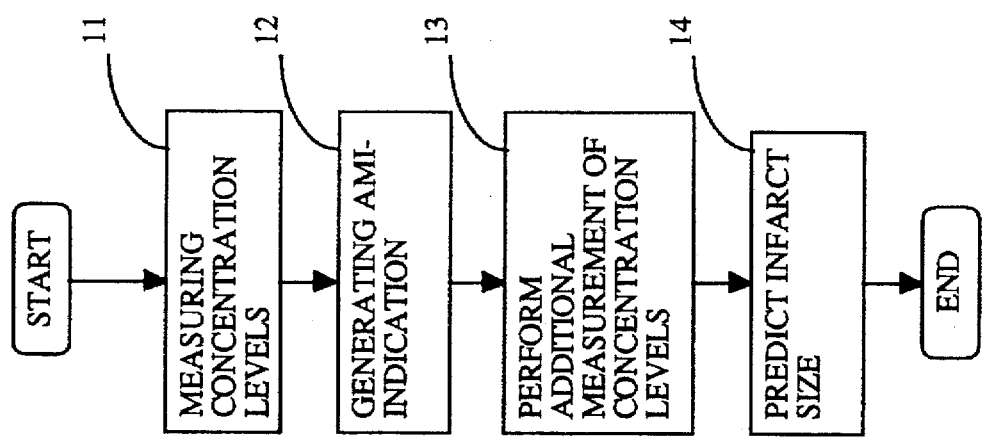
FIG. 2 is a schematic flow diagram of a method for detection of AMI and infarct size prediction in accordance with a first main aspect of the invention.

FIG. 2 is a schematic flow diagram of a method for detection of AMI and infarct size prediction in accordance with a first main aspect of the invention. In step 11, concentration levels of at least two biochemical markers of AMI in plasma of a patient are measured. In step 12, an indication of AMI is generated based on the measured concentration levels and first empirical data comprising concentration levels obtained from previous patients with AMI/non-AMI and a pre-classification of the presence/absence of AMI in these previous patients. In step 13 an additional measurement of concentration levels of the biochemical AMI-markers is performed. Next, in step 14 the infarct size is predicted based on the concentration levels obtained from the last measurement of step 11 and the additional measurement of step 13 and second empirical data comprising concentration levels obtained from previous patients with different infarct sizes and a pre-classification of the infarct sizes of the previous patients.

However, if measurements of concentration levels have been executed at two or more time instances in step 11, then it is possible to use the concentration levels obtained in the two last measurements of step 11 to predict the infarct size. Hence, in this alternative embodiment, step 13 is omitted.

If a diagnosis or detection of acute myocardial infarction in a patient together with a prediction of the size of the infarct is to be used as a decision support for possible thrombolytic treatment, then the detection and prediction generally have to be completed within the first hours from admission of the patient (the exact timing of course depends on the individual patient). For this reason, and in accordance with the first main aspect of the invention, the concentration levels are measured at at least two different time instances within 3 hours from admission of the patient.

Figure 3:
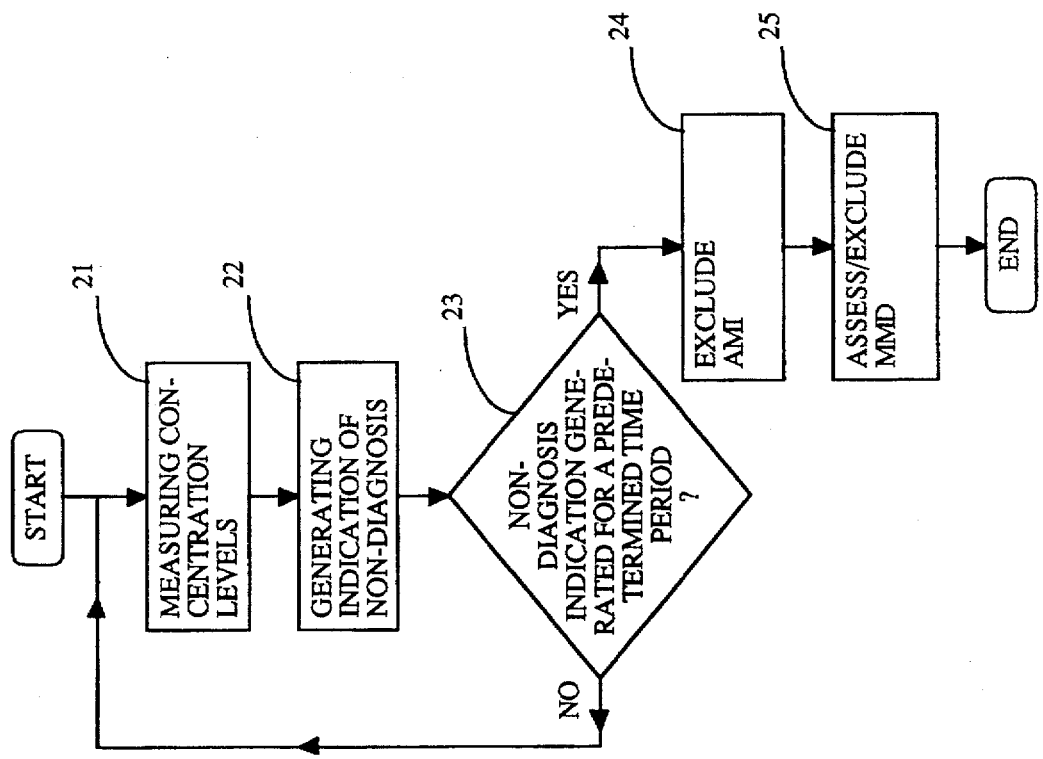
FIG. 3 is a schematic flow diagram of a method for exclusion of AMI and assessment/exclusion of MMD in accordance with a second main aspect of the invention.

FIG. 3 is a schematic flow diagram of a method for exclusion of AMI and assessment/exclusion of MMD in accordance with a second main aspect of the invention. In step 21, concentration levels of at least two biochemical markers of AMI in plasma of a patient are measured. In step 22, an indication of non-diagnosis is generated based on the measured concentration levels and first empirical data comprising concentration levels obtained from previous patients with AMI/non-AMI and a pre-classification of the presence/absence of AMI in these previous patients. A test (step 23) is performed to check if the non-diagnosis indication has been generated for a predetermined period of time, e.g. 3 hours from the initial measurement. The length of the predetermined period of time that is used in the test of step 23 is set based on empirical knowledge about the predictive values for non-AMI assessment such that a reliable non-AMI assessment can be made with a given level of significance. If NO in step 23, the method starts over again at step 21 with a further measurement of the concentration levels according to the predetermined measurement timing. Now, step 22 is executed using these new concentration levels, or alternatively an accumulative set of concentration levels comprising the initial concentration levels and the concentration levels obtained from the further measurement, and so on. If YES in step 23, then AMI is excluded (step 24) and possible minor myocardial damage in the patient is assessed/excluded in step 25.

It is obvious that optionally step 25 may be omitted such that a method directed only towards exclusion of AMI is provided.

The same general principles as for the overall method described in connection with FIG. 1 apply for the methods according to the first and second main aspect of the invention.

For a better understanding of the present invention and its advantages a detailed implementation of a preferred embodiment of the present invention will now be described.

PREFERRED EMBODIMENT

Figure 4:
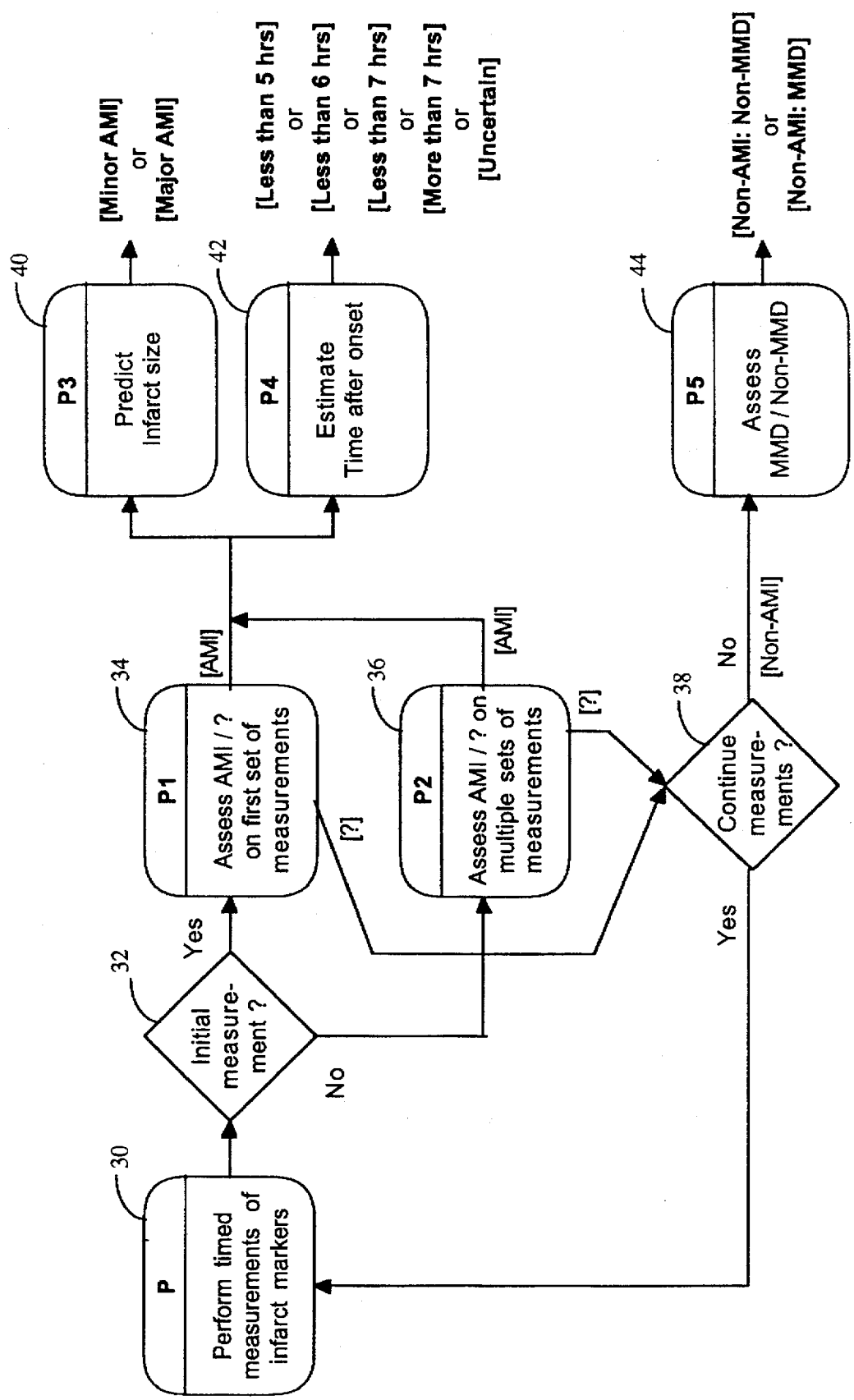
FIG. 4 is a top-level data flow diagram where the computational processes and the data flows are indicated.

A first preferred embodiment of the method of the present invention utilizes a combination of timed serial measurements of the concentration of myoglobin, CK-MB and cardiac troponin-T in plasma. The method is mainly implemented in a computer system designed in a modular fashion, where each module performs a specific task of computation. FIG. 4 is a top-level data flow diagram where the computational processes and the data flows are indicated. The leftmost process 30 represents timed measurements of infarct markers in plasma samples from the patient. These measurements can be performed with use of commercially available decentralized instruments with sufficiently short turnaround time for analysis, preferably less than 20 min. (e.g. the Opus analyzer from Behringwerk). The result of these measurements, plasma-mass concentration values of myoglobin, CK-MB and troponin-T, are taken as input to modules that are used for the detection of AMI. Different computational methods are used depending on whether the measurement is the first one, in module P1/34, from that patient or not, in module P2/36. If AMI is detected, the system makes a prediction of the infarct size in module P3/40 and an estimate of the time that has elapsed since onset of infarction in module P4/42. If, however, AMI is not detected after a specified optimized period of monitoring 38, AMI is excluded from the list of possible diagnoses. In this case the remaining task for the system is to make an assessment of whether the patient is suffering from a minor myocardial damage (MMD). This assessment is done in module P5/44.

The plasma-concentration values of the biochemical markers, measured in $\mu g/L$, are initially normalized to a comparable scale by dividing the measured values with the corresponding upper reference limits (URL=mean+2 standard deviations (SD) of reference values for a reference sample group of healthy individuals):

$Myo=Myo\_meas/URL$ $CKMB=CKMB\_meas/URL$  (1-3)

$TnT=TnT\_meas/URL$

The URLs are equal to 90 $\mu g/L$ (male) and 57 $\mu g/L$ (female) for myoglobin; 8.0 $\mu g/L$ for CKMB and 0.2 $\mu g/L$ for TnT.

Figure 5:
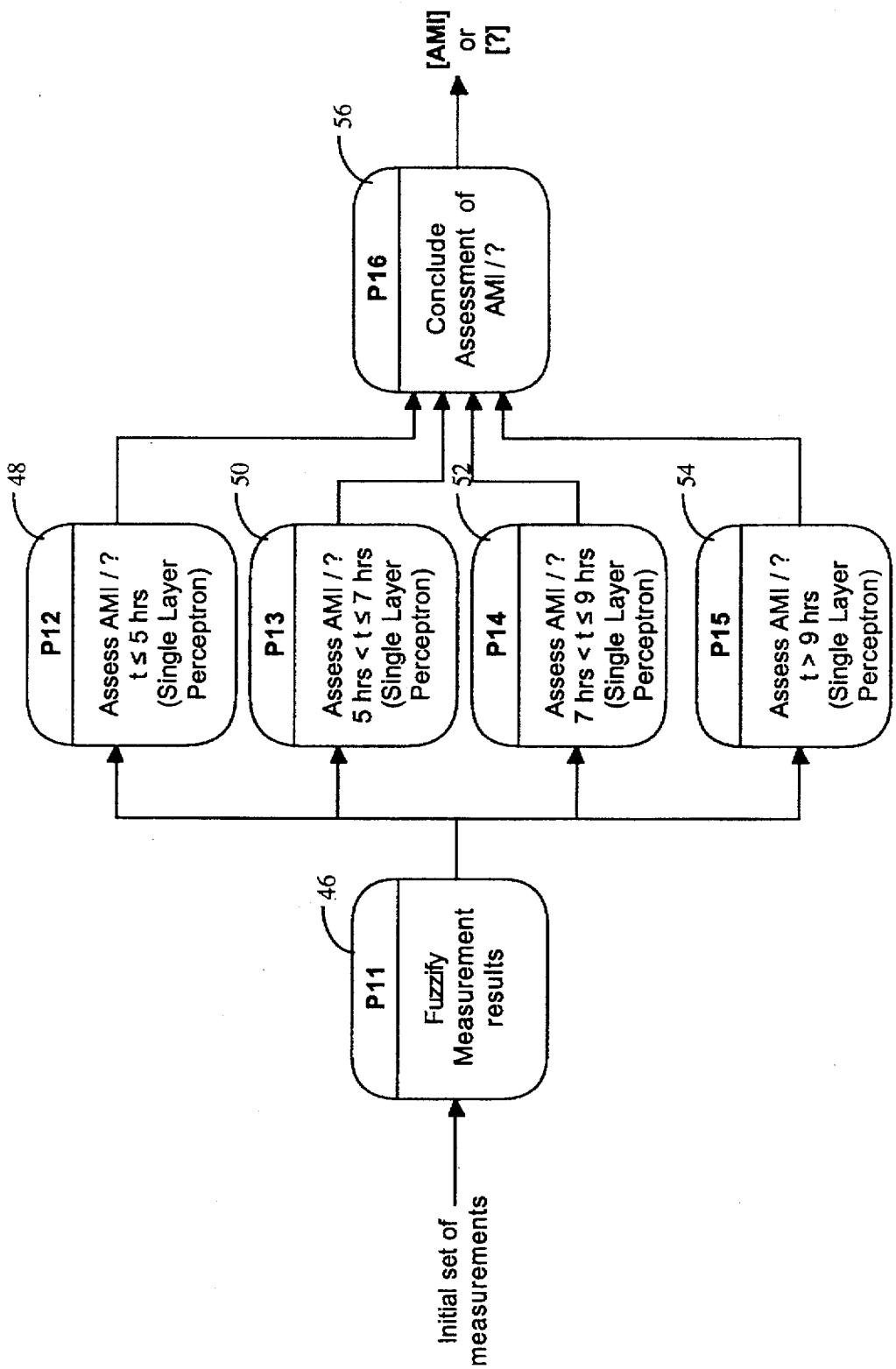
FIG. 5 is a child data flow diagram of module P1.
Figure 6:
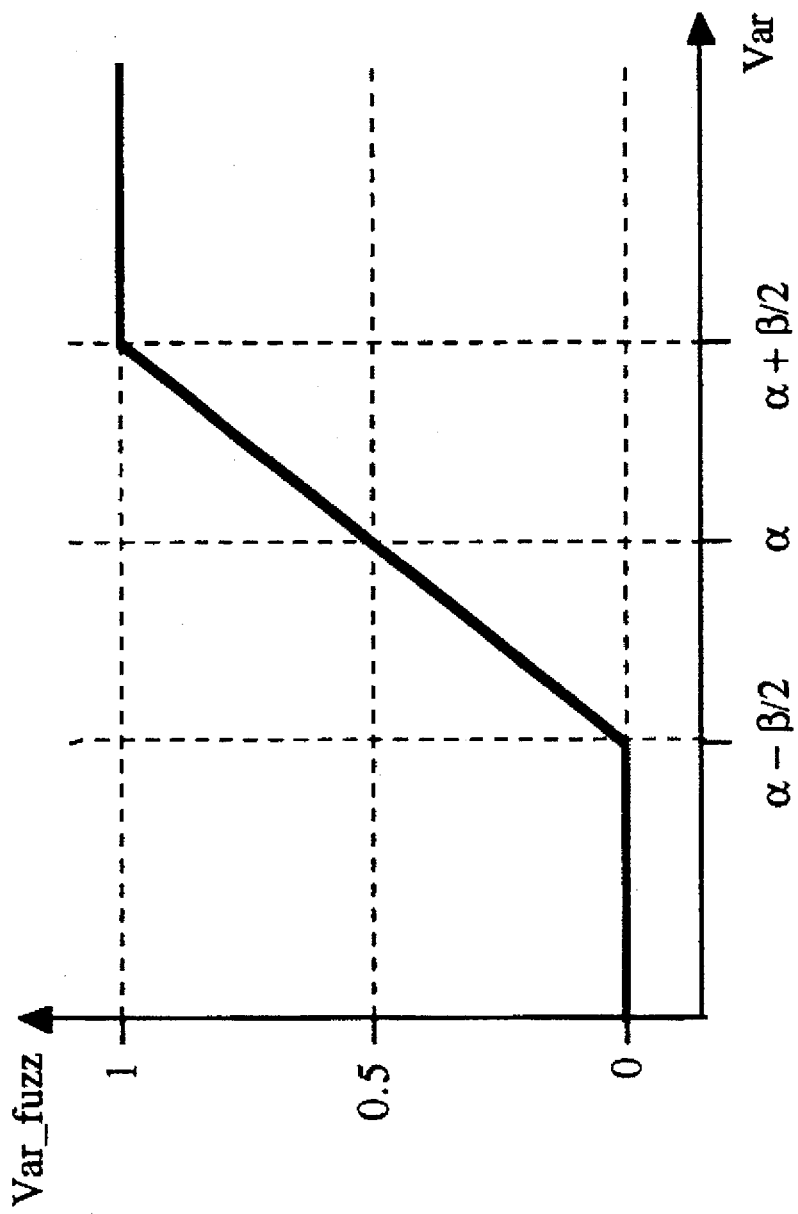
FIG. 6 is a schematic diagram of a piece-wise linear fuzzification function.

Module P1: Assessment of AMI on initial measurement using multiple single-layer perceptrons FIG. 5 is a child data flow diagram of module P1 (FIG. 4:34). It is implemented by a set of specialized perceptrons represented by the submodules P12–P15 48,50,52,54, that are trained to detect cases of AMI as they appear within four different time periods after the onset of symptoms. The rationale behind this time-structure of the P1 module (FIG. 4:34) is the fact that the financial and health costs and gains of true and false AMI classifications are highly time related during the first 12 hours after onset of infarction. Furthermore, the relative changes of marker concentrations are also pronounced during the same time period. In the preferred embodiment the following time periods are used: $t \leq 5$ hrs; $5 < t \leq 7$ hrs; $7 < t \leq 9$ hrs; $t > 9$ hrs. The input variables (Var: Myo, CKMB, TnT) are first fuzzified in module P11/46 using piece-wise linear functions that transform the values to the range [0, 1]. FIG. 6 is a schematic diagram of such a piece-wise linear function. The function in FIG. 6 is defined as follows:

$$Var\_fuzz = \begin{cases} 0, & Var < \alpha - \frac{\beta}{2} \\ \frac{(Var - \alpha)}{\beta} + \frac{1}{2}, & \alpha - \frac{\beta}{2} \leq Var \leq \alpha + \frac{\beta}{2} \\ 1, & Var > \alpha + \frac{\beta}{2} \end{cases} \quad (4\text{-}6)$$

where $\alpha$ and $\beta$ are given in Table 1.

TABLE 1

Constants used in the fuzzification of input variables to the neural networks.

| Input variable | α | β |
|---|---|---|
| Myo | 3 | 6 |
| CKMB | 2 | 4 |
| TnT | 1 | 2 |

Figure 7:
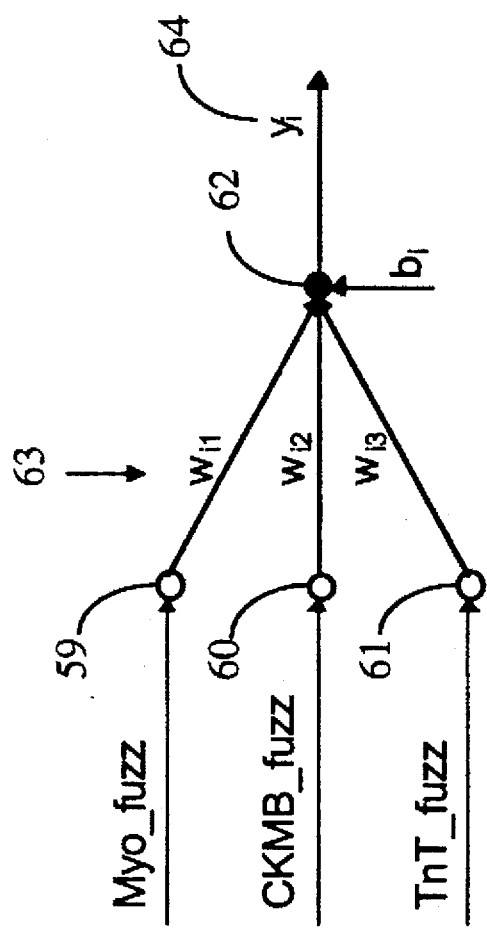
FIG. 7 illustrates the structure of the four single layer perceptrons that are used in module P1.

The values of the constants were set manually to achieve a separation between the preclassified example cases in the training set. Next, the fuzzified values are given as input to the four perceptrons (FIG. 5: 48,50,52,54). The structure of the four single layer perceptrons is illustrated in FIG. 7. The single layer perceptron comprises three input units 59,60,61 and one output unit 62. The output 64 from each one of the perceptrons (i=1,4) is given by:

$$y_i = F[w_{i1} Myo\_fuzz + w_{i2} CKMB\_fuzz + w_{i3} TnT\_fuzz + b_i] \quad (7a)$$
$$i = 1, 2, 3, 4$$

where the transfer function of the output unit 62 is given by:

$$F(x) = \frac{1}{1 + e^{-x}} \quad (7b)$$

$w_{i1}$ $w_{i2}$ $w_{i3}$ and $b_i$ (i=1, 2, 3, 4) represent the numerical weights 63 and biases resp. for the four single-layer perceptrons. Theoretically, one might use only the perceptron that is trained on data sets corresponding to the stated time after the onset of symptoms. However, considering the inaccuracy of the stated time estimate by the patient, the strategy is to use all the perceptrons in parallel. If the output from any one of these perceptrons should indicate an AMI, that is taken to be the actual state, and at the same time we obtain an indication of the accuracy of the stated time after onset. The decision rule for the conclusive assessment of AMI (FIG. 5:56) is defined by:

$$\delta(y) = \begin{cases} 1 & (\text{for } AMI) & \text{if } y \geq 0.5 \\ 0 & (\text{for ?}) & \text{if } y < 0.5 \end{cases} \quad (8a)$$

where $$y = \max\{y_1, y_2, y_3, y_4\} \quad (8b)$$

Module 2: Assessment of AMI on serial measurements

If AMI is not detected on the initial set of measurements, further monitoring of the infarct markers have to be performed before AMI can finally be excluded from the list of possible diagnoses. These continued measurements of infarct markers will form a set of time-series. In order to take into account the dimension of time thereby introduced, a new set of computational procedures are invoked.

Figure 8:
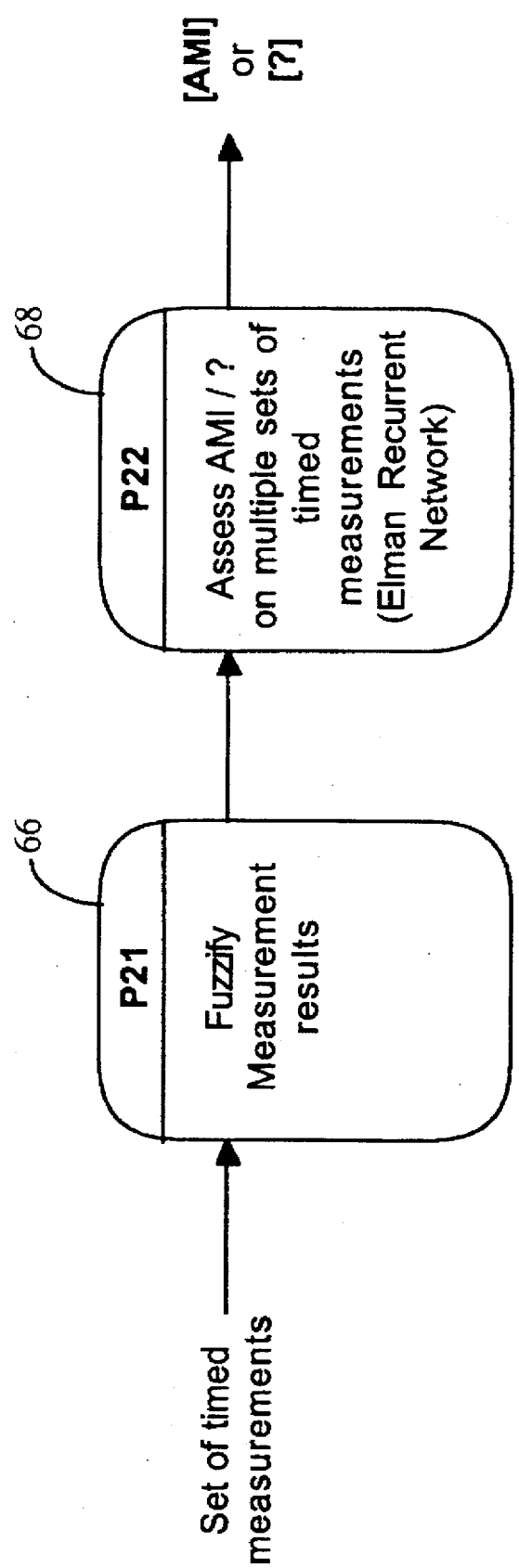
FIG. 8 is a child data flow diagram of module P2.
Figure 9:
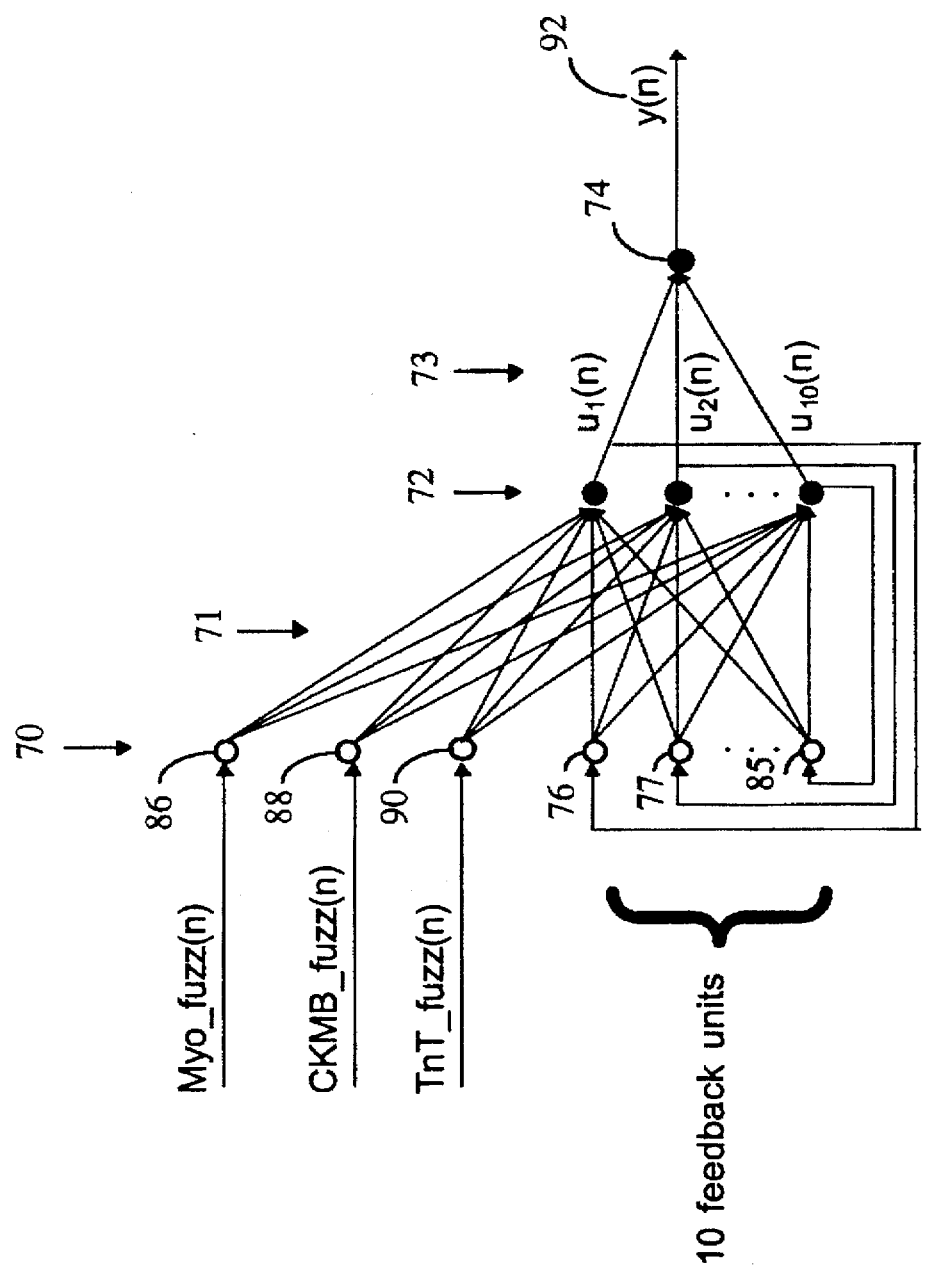
FIG. 9 illustrates an Elman neural network.

FIG. 8 is a child data flow diagram for module P2 (FIG. 4:36). First, a fuzzification is performed in submodule P21/66, according to eqs. 4–6 and Table 1 given above. Secondly, the fuzzified values are given as input to a classifier of submodule P22/68, using a neural network with a feedback connection, e.g. an Elman network. Elman networks are two-layer backpropagation networks, with the addition of a feedback connection from the output of the hidden layer to its input. Additional information can be obtained in the paper by J. L. Elman on 'Finding structure in time' (Cognitive Science 1990;14:179–211). This feedback path allows Elman networks to learn to recognize temporal patterns. FIG. 9 illustrates an Elman network with an input layer 70, a hidden middle layer 72 and an output unit 74. The input layer 70 includes 10 feedback units 76–85 in addition to three marker input units: Myo_fuzz 86, CKMB_fuzz 88, and TnT_fuzz 90.

The value calculated as output from the i:th unit $u_i$ (n) (for the n:th measurement) of the hidden middle layer 72 of the Elman network is given by the following recursive expression (n=1, 2, ... ):

$$u_i(n) = F_1 \left[ Myo\_fuzz \, w_{i1} + CKMB\_fuzz \, w_{i2} + \right. \quad (9a\text{-}9b)$$
$$\left. TnT\_fuzz \, w_{i3} + \sum_{k=4}^{13} u_i(n-1) w_{ik} + b_i \right]$$
$$u_i(0) = 0, \quad i = 1, 2, \ldots 10$$

where n is the current number of the set of measurements, and the transfer function of the ten units in the middle layer 72 is given by $$F_1(x) = \tan h(x) \quad (9c)$$

$w_{ik}$ and $b_i$ (i=1, 10; k=1, 13) are the numerical weights 71 and the biases resp. of the middle layer 72. The output value 92 from the network is:

$$y(n) = F_2 \left[ \sum_{i=1}^{10} u_i(n) w_i + b \right] \quad n = 1, 2, 3, \ldots \quad (9d)$$

where the transfer function of the output unit 74 is given by $$F_2(x) = x \quad (9e)$$

$w_i$ (i=1, 10) and b are the numerical weights 73 and the bias of the output unit 74. The network was trained to output "1" in cases of AMI, and "0" in cases of Non-AMI. The decision rule for measurement n is $$\delta(y(n)) = \begin{cases} 1 & (\text{for } AMI) & \text{if } y(n) \geq 0.5 \\ 0 & (\text{for ?}) & \text{if } y(n) < 0.5 \end{cases} \quad (10)$$
$$n = 2, 3, 4, \ldots$$

that is a positive test result ($\delta(y(n))=1$) is interpreted as the detection of AMI, whereas a negative test result ($\delta(y(n))=0$) indicates that further measurements are required, following a predetermined schedule.

Typically, measurements of infarct markers are performed every 30 minutes. At a certain time point (e.g. 3 hours after the first sample), the monitoring process is ended (FIG. 4:38). If the network still outputs [?], this is taken as an indication of Non-AMI, i.e. AMI is excluded as a possible diagnosis. If the monitoring process should result in a detection of AMI, then the computational method continues with sub-modules P3 (FIG. 4:40) and P4 (FIG. 4:42), in order to predict infarction size and to estimate the time since the onset of infarction. Should however the result be [Non-AMI], additional methods will be used to detect possible occurrence of a minor myocardial damage (FIG. 4:44).

Module P3: Prediction of infarct size

Figure 10:
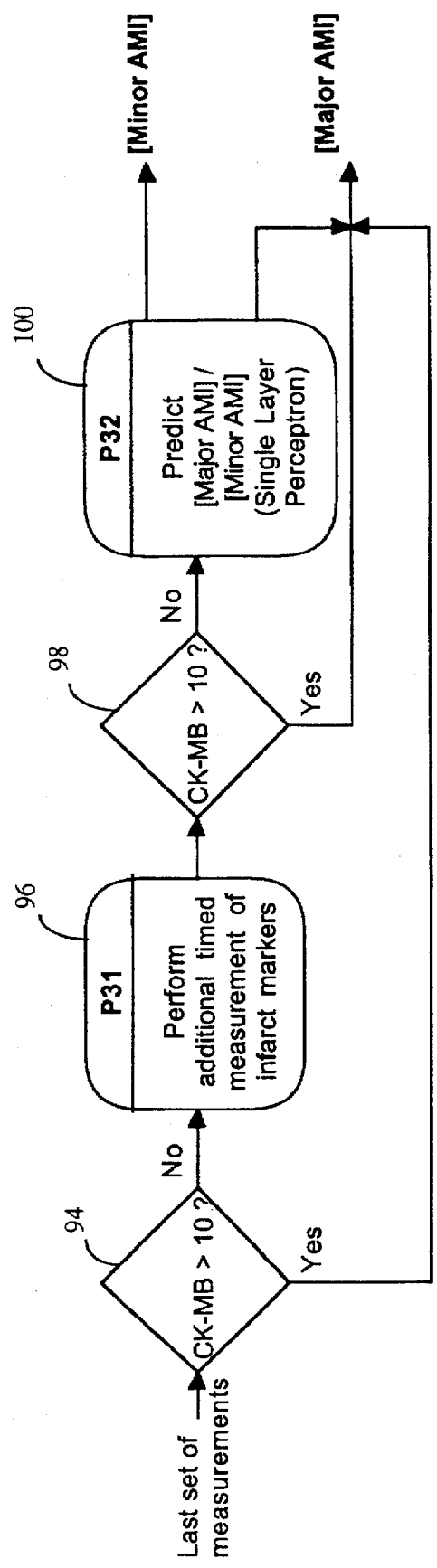
FIG. 10 is a child data flow diagram of process P3.

The objective for this module (FIG. 4:40) is to make an early prediction of the infarct size as being either 'Major' or 'Minor', requiring no more than one additional measurement of relevant infarct markers after the detection of AMI. FIG. 10 is a child data flow diagram of process P3. AMI was defined to be 'Major' if the measured peak value of CK-MB exceeded 80 mg/L (10 normalized units). Therefore, if the current measured value of CK-MB is greater than 10 normalized units in test 94, the AMI is classified as 'Major'. Otherwise, one additional measurement is performed in submodule P31/96. If both measured values of CK-MB are lower than 10 in test 98, submodule P32/100 is invoked to make a prediction of the infarct size.

Figure 11:
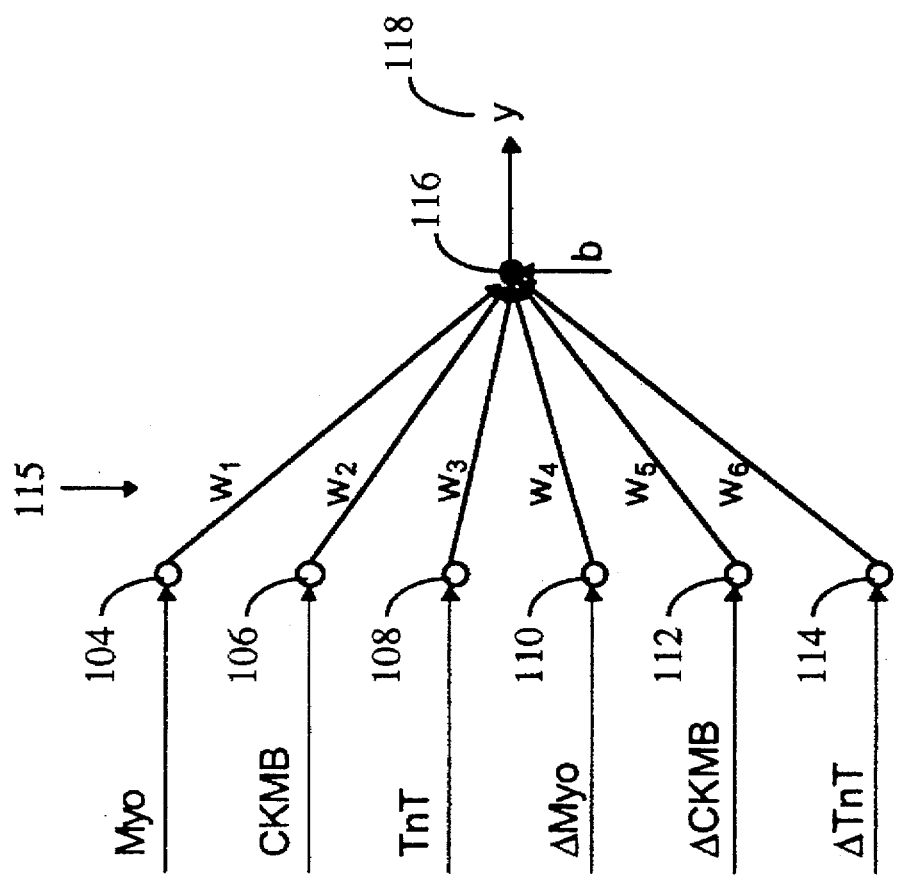
FIG. 11 illustrates the single-layer perceptron that is used for infarct size prediction.

FIG. 11 illustrates the single-layer perceptron that is used for predicting the infarct size. It has 6 input units 104,106, 108,110,112,114, requiring 2 consecutive sets of measurements of the infarct markers. Three of the input units 104,106,108 receive the normalized (but not fuzzified) values of the measured markers, while the remaining three units 110,112,114 receive their respective 2 point derivatives at that time instant (approximated by the difference of two consecutive values of the marker).

The output 118 from the perceptron is given by $$y=F[w_1 Myo+w_2 CKMB+w_3 TnT+w_4 \Delta Myo+w_5 \Delta CKMB+w_6 \Delta TnT+b] \quad (11a)$$

where $w_i$ (i=1, 6) and b are the numerical weights 115 and bias, respectively, and the transfer function of the output unit 116 is given by:

$$F(x) = \frac{1}{1+e^{-x}} \quad (11b)$$

The decision rule is defined by:

$$\delta(y) = \begin{cases} 1 & \text{(for Major } AMI\text{)} \quad \text{if } y \geq 0.5 \\ 0 & \text{(for Minor } AMI\text{)} \quad \text{if } y < 0.5 \end{cases} \quad (12)$$

Module P4: Estimation of time after onset of infarction

Figure 12:
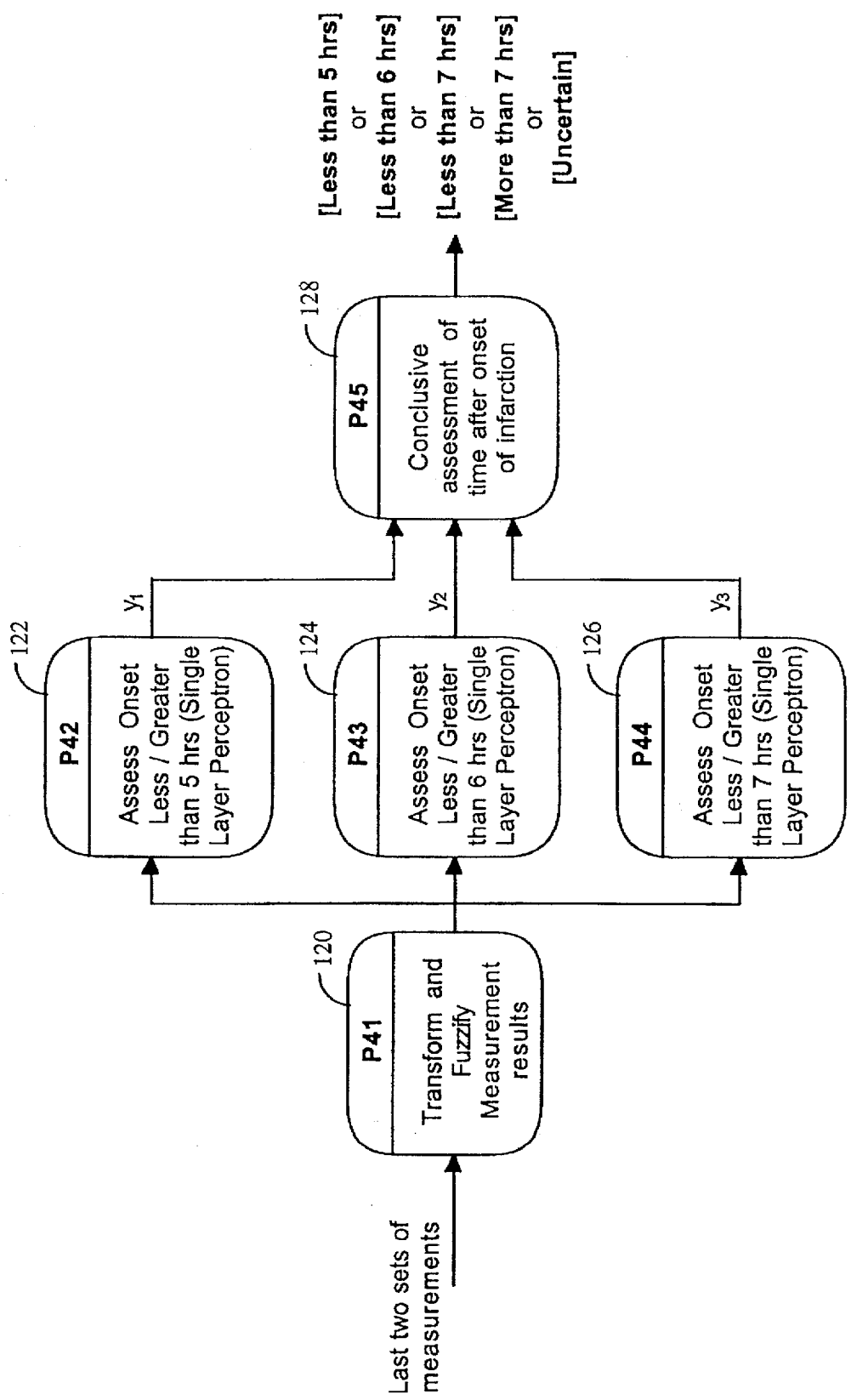
FIG. 12 is a child data flow diagram of module P4.

Together with an estimate of infarct size, the time that has elapsed since onset of infarction is an important piece of information on which the clinician can base a decision of eventual therapy. Considering the circumstance that the patients own estimates of times for onset of symptoms often can be uncertain, another set of three single layer perceptrons is applied to estimate the time from onset of infarction more objectively with use of the measured infarct markers ("second opinion"). FIG. 12 is the child data flow diagram of module P4 (FIG. 4:42) in which this functionality is implemented. It comprises three single-layer perceptrons represented by the submodules P42–44/122,124,126 trained to classify the time since onset of infarction as: less/greater than 5 hours; less/greater than 6 hours; and less/greater than 7 hours. Considering this procedure as a triple test, the outcomes from the conclusive assessment made in submodule P45/128 are defined as [Less than 5 hrs], [Less than 6 hrs], [Less than 7 hrs], [More than 7 hrs] and [Uncertain] respectively.

Figure 13:
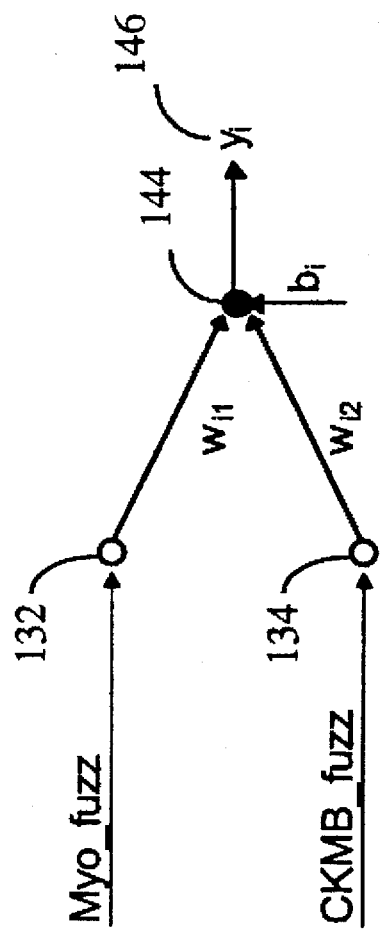
FIG. 13 illustrates the structure of the single layer perceptrons used for estimating the time after onset of symptoms.

FIG. 13 illustrates the structure of each one of the single layer perceptrons used for this purpose. There are 2 input units 132,134 in the first layer with the normalized and fuzzified values of Myo and CKMB as input variables. The fuzzification (FIG. 12:120) is achieved by piece-wise linear functions that transform the individual input variables to the range [0, 1] according to eqs. (4–6) given above and Table 2 below:

TABLE 2

Constants used in the fuzzification of the input variables to the neural networks.

| Input variable | α | β |
|---|---|---|
| Myo | 7.5 | 15 |
| CKMB | 25 | 50 |

The output 146 from the i:th perceptron is given by $$y_i = F[w_{i1} Myo\_fuzz + w_{i2} CKMB\_fuzz + b_i] \, i=1, 2, 3 \quad (17a)$$

where the transfer function of the output unit 144 is $$F(x) = \frac{1}{1+e^{-x}} \quad (17b)$$

and $w_{i1}$, $w_{i2}$ and $b_i$ (i=1, 2, 3) are the numerical weights and biases, respectively, of the perceptrons. The decision rules of module P45 (FIG. 12:128) are defined by:

$$\delta(y_i) = \begin{cases} 1 & \text{(Onset Less Than } X_i \text{ hours)} \quad \text{if } y_i \geq 0.5 \\ 0 & \text{(Onset Greater Than } X_i \text{ hours)} \quad \text{if } y_i < 0.5 \end{cases} \, i=1,2,3 \quad (18)$$

$X_1=5$ hrs, $X_2=6$ hrs and $X_3=7$ hrs, and Table 3. The final estimate is generated by the decision table given below.

TABLE 3

Decision table in sub-module P45

| δ (y1) | δ (y2) | δ (y3) | Decision |
|---|---|---|---|
| 1 | 1 | 1 | Onset Less Than 5 hrs |
| 1 | 1 | 0 | Uncertain |
| 1 | 0 | 1 | Onset Less Than 5 hrs |
| 1 | 0 | 0 | Uncertain |
| 0 | 1 | 1 | Onset Less Than 6 hrs |
| 0 | 1 | 0 | Uncertain |
| 0 | 0 | 1 | Onset Less Than 7 hrs |
| 0 | 0 | 0 | Onset Greater Than 7 hrs |

As should be understood by those skilled in the art, a further biochemical marker, e.g. troponin-T, is easily incorporated into this module. In such an embodiment, the structure of the single layer perceptrons will have 3 input units in the first layer instead of 2.

Module P5: Assessment of Minor Myocardial Damage

Figure 14:
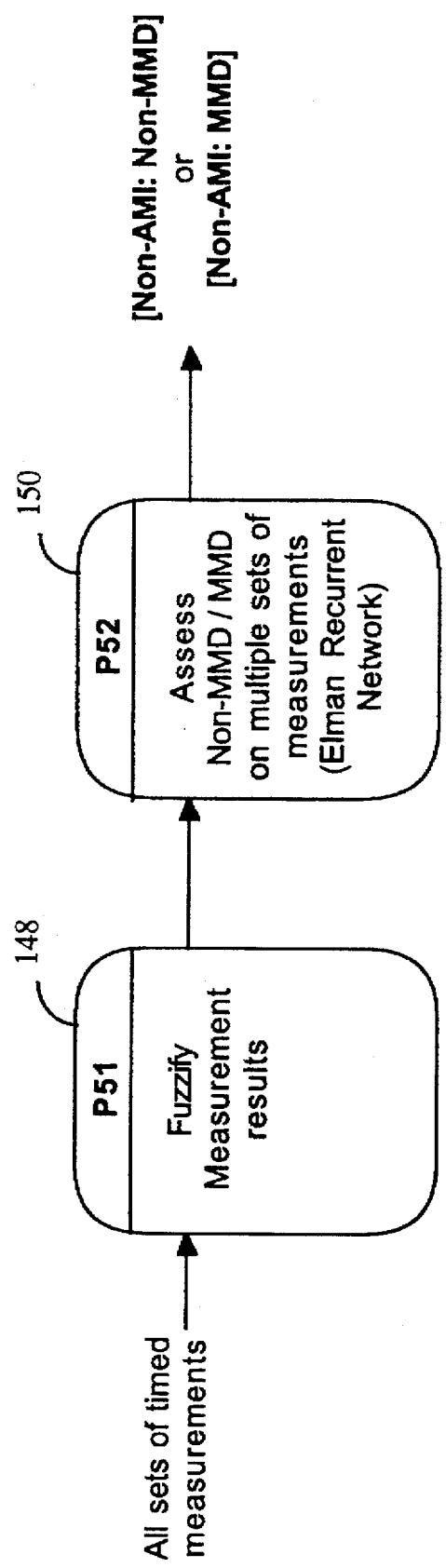
FIG. 14 is a child data flow diagram of module P5.

If AMI is excluded, a remaining task for a decision is to detect the possible presence of a minor myocardial damage, MMD. Several measurements of the markers have been gathered during the monitoring process; the optimum number was found to be 7. The computational module P5 (FIG. 4:44) uses an Elman recurrent neural network trained to detect typical marker-patterns of minor myocardial damage. FIG. 14 is the child data flow diagram of module P5 composed of one process for fuzzification 148 and another for the assessment of Non-MMD/MMD 150.

The structure of the Elman network is identical to the network used for detection of AMI in P22 (see FIG. 9). The input layer of the Elman network 70 has three inputs 86,88,90 for the markers (myoglobin, CK-MB, Tn-T) and 10 feedback units 76–85. The network is trained to output '1' if MMD is present and '0' in case of Non-MMD. The time-series of infarct markers are first fuzzified in submodule P51 (FIG. 14:148) to a range [0, 1] using eqs. 4–6 and Table 1 given above, and then given as input to the Elman network of submodule P52 150. The output y(n) (FIG. 9:92) from the network is defined by equations 9a–9e.

The decision rule is defined by:

$$\delta(y(7)) = \begin{cases} 1 & (\text{for } MMD) & \text{if } y(7) \geq 0.5 \\ 0 & (\text{for } Non\text{-}MMD) & \text{if } y(7) < 0.5 \end{cases} \quad (19)$$

Training of the single-layer perceptrons and Elman recursive neural networks
Hardware and software The system was implemented on a Macintosh IIfx using the Matlab® software package v4.2 together with the "Neural Network Toolbox v2.0". Several algorithms (implemented as "m-files") for training the networks were modified in the toolbox to account for a new object function of minimization and improved criteria for determining the optimal number of training epochs in the learning process.
Object function Training of a neural network is achieved by optimizing an object function providing a measure of the deviation between the neural network classification and the "golden standard" preclassification of a number of representative example cases in a training set. A standard choice of such a function is the "sum of squared residuals", which is minimized during the training. In the present invention, the net gain of weighted true and false classifications is used as an object function:

$$\text{Net gain} = TP \cdot \text{gain } TP + TN \cdot \text{gain } TN - FP \cdot \text{cost } FP - FN \cdot \text{cost } FN \quad (20)$$

where TP, TN, FP and FN are the number of 'true positives', 'true negatives', 'false positives' and 'false negatives', respectively. The costs and gains are the respective weights attributed to making such a classification. They may be expressed in terms of loss and gain of life expectancy, or in relative units.

The Net gain-function can be expressed as:

$$NG = \sum_{i=1}^{n} \{f(d_i, y_i) \cdot cg(d_i, y_i, t_i)\} \quad (21)$$

where n is the number of cases in the training set; $f(d_i, y_i)$ is a function determining the extent to which the neural network output $y_i$, corresponds to the golden standard classification $d_i$, of the i:th case in the training set. It is given by the expression:

$$f(d_i, y_i) = (1-2y_i)(1-2d_i) - 1.23\, f(d_i, y_i) \leq 1 \quad (22)$$

where $$d_i = \begin{cases} 0 & (\text{Negative golden standard classification}) \\ 1 & (\text{Positive golden standard classification}) \end{cases} \quad (23)$$

and $y_i$ is given by various expressions defining the output functions, cf. equations 7a, 9d, 11a, 17a.

The gains and costs associated with a classification of a training case as being either positive (y>0.5), or negative (y≦0.5) given the golden standard classification d, are defined in a set of tables of the following type, for specified time-intervals after onset of infarction:

TABLE 4

The costs/gains- function cg (d, y, t) defined as a matrix with constant numerical weights.

| Neural Net Output | Golden Standard classification | |
|---|---|---|
| | d = 0 (negative) | d = 1 (positive) |
| y < 0.5 (negative) | Gain TN | Cost FN |
| y > 0.5 (positive) | Cost FP | Gain TP |

The back-propagation algorithm is applied which gives a rule for updating the j:th weight of the i:th unit and its bias during the training process:

$$w_{ij}(k+1) = w_{ij}(k) + \alpha \frac{\partial NG}{\partial w_{ij}} \quad (24a)$$

$$b_i(k+1) = b_i(k) + \beta \frac{\partial NG}{\partial b_i} \quad (24b)$$

where k is the number of the current iteration in the training set.
Alternative ways of embodying the invention Although three specific AMI-markers are used in the first preferred embodiment of the invention, the scope of the invention is not limited thereto. It is possible to use only two biochemical markers of AMI. In fact, the general requirement is to use at least two AMI-markers. Hence, four markers or more can also be used. In addition, other biochemical markers of AMI than those mentioned above, such as cardiac proteins in general, are possible to use. Specific examples of alternative AMI-markers are lactate dehydrogenase, glycogen phosphorylase BB and heart-type fatty acid binding protein (h-FABP).

The measurements of the concentration levels of the biochemical markers do not have to be performed with equidistant time intervals, but can, by way of example, be executed according to the following timing example: 0, 15, 30, 60, 120, 180 (minutes after admission).

In accordance with the general idea behind the neural network structure of module P1, the network should comprise at least two perceptrons, each one of which is trained to detect AMI within an individual time after onset of symptoms.

According to a first alternative embodiment, the network structure of module P1 is used not only for the initially measured concentration levels of the biochemical markers, but for concentration levels measured at each subsequent time instance of the predetermined measurement schedule. In this first alternative embodiment, the neural network of module P2, i.e. the Elman network, is not used at all, or the P1-neural network and the P2-neural network are used in parallel.

When it comes to MMD-assessment, in the preferred embodiment, all sets of measurements of marker concentrations are sent to the Elman network of module P5. However, in order to reduce the time required for assessing MMD/non-MMD, a smaller number of measurement sets may be used. Hence, there is a trade-off between reliability and required time.

The Elman network of module P2 and P5 is used for recognizing temporal patterns, but other suitable two-layer neural networks with a feedback connection are also possible to use for this purpose.

Regarding the estimation of a time period within which onset occurred, the general idea is to use at least one single layer perceptron trained to classify the time since onset. Preferably, however, more than one perceptron is used and each one of these perceptrons generates an individual time estimate. Next, the individual time estimates are sent to a decision table for generating a final estimate of a time period within which the onset of infarction occurred.

The preprocessing, i.e. the normalization and/or the fuzzification, of the determined concentration levels of the biochemical markers as given above in connection with the preferred embodiment is not intended to limit the scope of the invention, and can be modified. In fact, in an alternative embodiment of the invention, the preprocessing of the concentration levels is omitted and instead one or more hidden layers are added to the neural network structures. The actual number of units in the hidden layer is selected by empirical testing. A single additional hidden layer is capable of approximating any continuous function as described in the book Introduction to the Theory of Neural Computation by Hertz, Krogh and Palmer, Addison-Wesley (1991). However, this solution with a further hidden layer is realized at the expense of increased neural complexity and in general also reduced reliability.

As should be understood by those skilled in the art, different combinations, other than those given explicitly above, of the technical features described in the detailed description of embodiments may be realized. By way of example, detection of AMI, prediction of infarct size and time estimation may be combined.

Furthermore, the inventive methodology and neural network arrangements for predicting the infarct size, estimating the time after onset of infarction and assessing MMD/non-MMD can be utilized independently from each other and independently from the AMI-detection/exclusion.

AMI-detection apparatuses

In the following, four schematic block diagrams of apparatuses for early detection of AMI in accordance with different aspects of the invention will be described.

Figure 15:
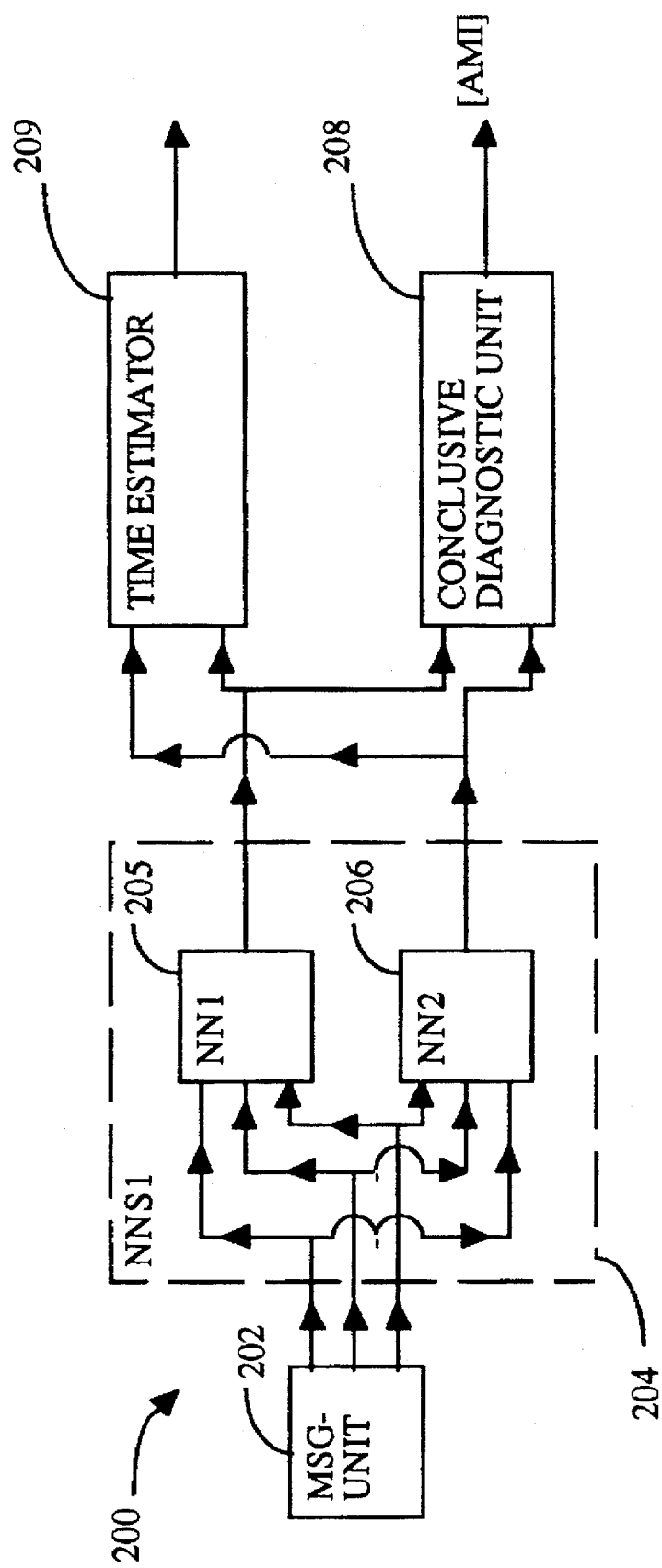
FIG. 15 is a schematic block diagram of an apparatus for detection of AMI according to an aspect of the invention.

FIG. 15 is a schematic block diagram of an apparatus for detection of AMI according to one aspect of the invention. The detection apparatus 200 comprises a measuring- and signal generating (MSG) unit 202, a first neural network structure 204 and a conclusive diagnostic unit 208. The measuring part of the MSG-unit 202 analyzes blood samples taken from a patient and determines the concentration levels of at least two, preferably three, biochemical markers. The measuring part of MSG-unit 202 is preferably implemented as described above in connection with the preferred embodiment of the invention. Assume by way of example that concentration levels of myoglobin, CK-MB and troponin-T are measured. These concentration levels are generally normalized according to eq. 1–3 described above, and fuzzified according to eq. 4–6. The normalization and fuzzification are executed in the software implemented signal generating part of the MSG-unit 202. The output signals of the MSG-unit 202 are concentration level representing signals. If levels of three markers are measured, then three output signals are generated. The output signals of the MSG-unit 202 are sent to the first neural network structure 204. The first neural network structure (NNS1) 204 is trained with empirical data comprising concentration levels obtained from previous patients with AMI/non-AMI and a pre-classification of the presence/absence of AMI in said previous patients to detect marker-patterns of AMI. The first neural network structure 204 generally comprises at least two neural networks. Assume for reasons of simplicity that NNS1 204 comprises two neural networks 205, 206. Each neural network 205/206 is trained to detect AMI within an individual defined time period after onset of symptoms of infarction for generating an individual indication of AMI/non-diagnosis. Examples of individual defined time periods are 0–5 hours and 5–7 hours. Preferably, NNS1 204 is similar or identical to that used in module P1 of the preferred embodiment of the invention (FIG. 5), and the neural networks 205, 206 are single layer perceptrons similar to that of FIG. 7. Next, the individual indications of AMI/non-diagnosis generated by NNS1 204 are sent to the conclusive diagnostic unit 208 which generates a conclusive indication of AMI based on the individual indications. In general, the conclusive AMI-indication is generated according to eq. 8a–b described above.

In another embodiment, the detection apparatus 200 further comprises a device 209 for generating an estimate representing a time period within which onset of infarction occurred based on the individual defined time periods and the individual indications of AMI/non-diagnosis. By way of example, if the neural network that is trained to detect AMI within the time period 5–7 hours generates an indication of AMI, while the other neural network that is trained to detect AMI within the time period 0–5 hours generates an indication of non-diagnosis, this is taken as a sign that the onset of infarction occurred within 5 to 7 hours after onset of symptoms of infarction.

Figure 16:
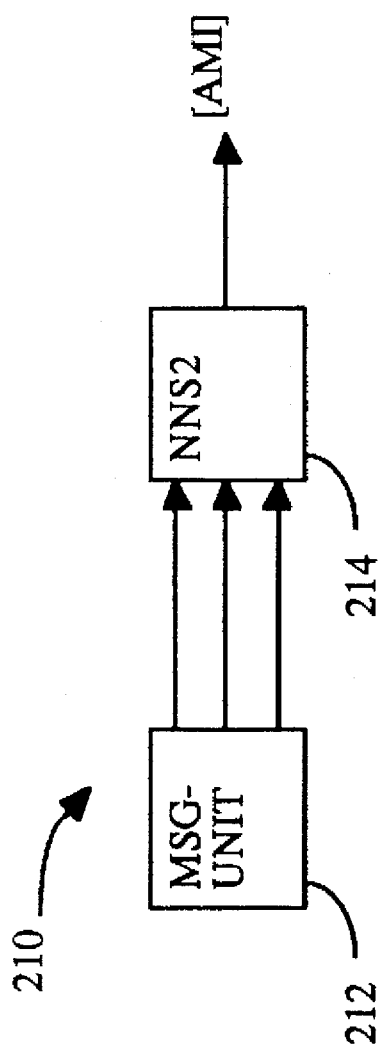
FIG. 16 is a schematic block diagram of an apparatus for detection of AMI according to another aspect of the invention.

FIG. 16 is a schematic block diagram of an apparatus for early detection of AMI according to another aspect of the invention. The apparatus 210 comprises a measuring- and signal generating (MSG) unit 212 and a second neural network structure (NNS2) 214. Preferably, the MSG-unit 212 is identical to the MSG-unit 202 of FIG. 15. The second neural network structure 214 is a two layer back-propagation neural network with a feedback connection, preferably an Elman recurrent neural network as the one described in connection with FIG. 9. The second neural network structure 214 or the Elman network is trained with empirical data comprising concentration levels obtained from previous patients with AMI/non-AMI and a pre-classification of the presence/absence of AMI in said previous patients to detect marker-patterns of AMI. The concentration level representing signals of MSG-unit 212 are sent to the Elman network 214. The Elman network 214 generates an indication of AMI when it recognizes a temporal concentration level pattern that is characteristic of acute myocardial infarction.

Figure 17:
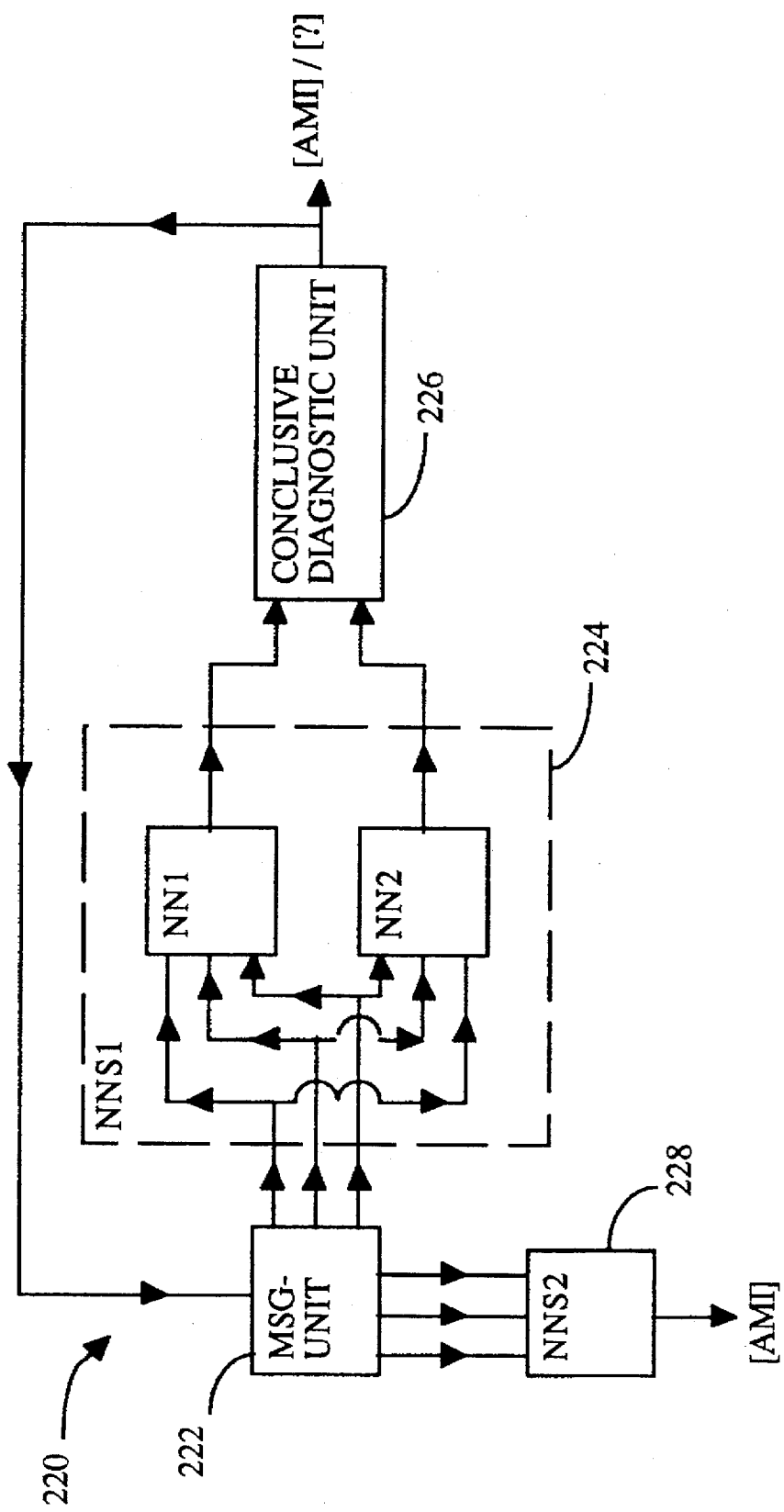
FIG. 17 is a schematic block diagram of an apparatus for detection of AMI according to yet another aspect of the invention.

FIG. 17 is a schematic block diagram of an apparatus for detection of AMI according to yet another aspect of the invention. The detection apparatus 220 comprises a measuring- and signal generating (MSG) unit 222, a first neural network structure (NNS1) 224, a conclusive diagnostic unit 226 and a second neural network structure (NNS2) 228. In general, the MSG-unit 222, the first neural network structure 224 and the conclusive diagnostic unit 226 are identical or similar to the units of FIG. 15, and the second neural network structure 228 is identical or similar to that of FIG. 16. The first neural network structure 224 is responsive to the initial concentration level representing signals of the MSG-unit 222. These signals represent the initially measured concentration levels of the biochemical markers. The first neural network structure 224 together with the conclusive diagnostic unit 226 generates a first indication of AMI/non-diagnosis. If an AMI-indication is generated, AMI is detected and the process is completed. However, if a non-diagnosis indication is generated, then the second neural network structure 228 is activated (a feedback connection from the conclusive diagnostic unit 226 provides MSG-unit 222 with information of the non-diagnosis indication). The second neural network structure 228 generates a second indication of AMI when it recognizes a temporal concentration level pattern that is characteristic of AMI.

Figure 18:
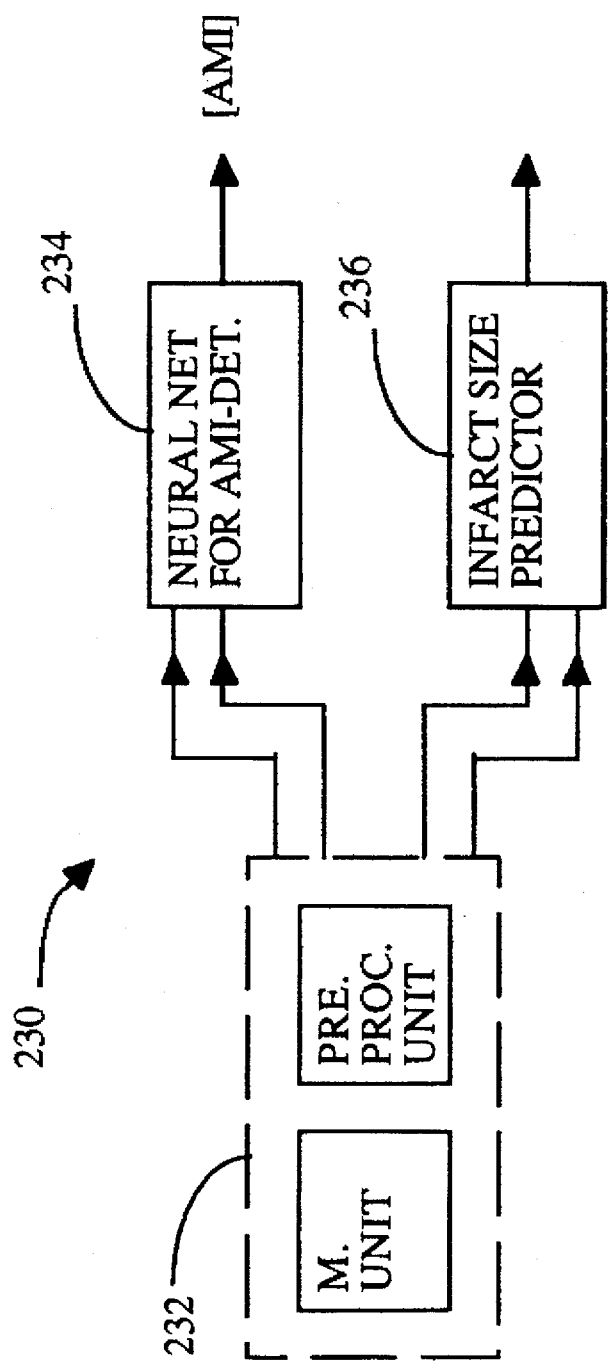
FIG. 18 is a schematic block diagram of an apparatus for detection of AMI and for early infarct size prediction.

FIG. 18 is a schematic block diagram of an apparatus for detection of AMI and for early infarct size prediction. The detection and prediction apparatus 230 comprises a measuring unit 232 and a neural network structure 234 for detecting AMI and a device for predicting the infarct size 236. The measuring unit 232 analyzes blood samples taken from a patient and determines the concentration levels of at least two, preferably three, biochemical markers, and is preferably implemented as described above in connection with the preferred embodiment of the invention. The neural network structure 234 generates an indication of AMI based on a first predetermined set of the concentration levels measured by the measuring unit 232 and first empirical data comprising concentration levels obtained from previous patients with AMI/non-AMI and a preclassification of the presence/absence of AMI in said previous patients. The neural network structure 234 is trained with the first empirical data to detect marker-patterns of AMI. The infarct size predicting device 236 makes a prediction of the infarct size based on a second predetermined set of said concentration levels and second empirical data comprising concentration levels obtained from previous patients with different infarct sizes and a preclassification of the infarct sizes of said previous patients. Preferably, the infarct size predictor 236 is implemented by a further neural network structure trained with the second empirical data to detect marker-patterns of different infarct sizes.

Optionally, the measuring unit 232 further comprises a unit for preprocessing the determined concentration levels. The preprocessing generally includes normalization and fuzzification as described above. If the concentration levels are preprocessed, then a good choice for the neural network implementations is given in the following: By way of example, the neural network structure 234 is identical to that used in module P1 of the preferred embodiment of the invention, and the further neural network structure 236 is identical to that used in module P3 of the preferred embodiment.

If no preprocessing is performed, the neural network structures are provided with further hidden layers such that the preprocessing functionality is performed implicitly by the neural network structures themselves.

RESULTS AND DISCUSSION

The implications of the approach and methods of the present invention are shown in Tables 5-9. The results were obtained from an evaluation on patients representative for the CCU population except that candidates for thrombolytic treatment according to current criteria were excluded. More detailed information about the patient material is found in paper by B Lindahl et al. in Coronary Artery Disease 1995; 6:321-328.

The validity of the computer method was assessed by calculating the diagnostic sensitivity, specificity and positive and negative predictive values for the detection of each condition (AMI, MMD and Non-AMI) versus the others, and for cases of AMI, detection of 'Major AMI' as opposed to 'Minor AMI'. In addition, the performance of the computer method was compared to the performance of three experienced clinicians.

Although the patient material is unique with the early frequent blood sampling, the number of patients is limited, in both the learning and test sets. However, the results are indicative of the potential benefit of the present invention in the early management of patients with acute chest pain.

Detection of AMI

The computer method (P1, P2) detected AMI earlier than the clinicians (Table 5). An average time of 6 minutes was required for the computer method whereas the clinicians required 20 minutes on the average. Sensitivity, specificity and predictive values for detection of AMI are not significantly different for the computer method and the clinicians (Table 6). The sensitivity for both the computer method and the clinicians are 1.00, that is, all cases of AMI were correctly diagnosed. Positive and negative predictive values for both the computer method and the clinicians are high.

Detection of Non-AMI with MMD

The computer method (P5) detected MMD faster and with a higher sensitivity and a higher positive predictive value than the clinicians. The computer method required on the average 180 minutes to make a correct assessment whereas the clinicians required 573 minutes (Table 5). The computer method correctly assessed MMD in 5 of 8 patients whereas for the clinicians, the best single result was 3 correct assessments of MMD of a total of 8 patients. The positive predictive value for the computer method was 1.00 and for the clinicians 0.83 on the average (Table 6).

Detection of Non-AMI without MMD—Exclusion of AMI and MMD

The clinicians excluded AMI and MMD somewhat faster than the computer method (130 minutes for the clinicians on the average, and 180 minutes for the computer method). However, the specificity and the positive predictive value for the computer method were higher than for the clinicians (Table 6). The computer method incorrectly assessed Non-AM/without MMD for one patient suffering from MMD, whereas the clinicians for the same task misclassified between 3 and 5 patients, all suffering from MMD.

Prediction of infarct size

The computer method (P3) made a correct prediction of major/minor infarct size earlier than the clinicians (Table 7). The computer method needed approximately half an hour of monitoring time to make a correct prediction while the clinicians required 2 and 4 hours on the average, for a correct prediction of major and minor infarctions, respectively. The computer method and the clinicians did not differ significantly in terms of sensitivity, specificity and positive and negative predictive values (Table 8).

Estimation of time from onset of infarction

The computer method (P4) estimates the time from onset of infarction based only on the time series of measured biochemical markers as described above. Sensitivity, specificity and predictive values for the computer method are showed in Table 9. The positive predictive values are high, 0.92/0.90/0.81 for tests '<5 hrs?'/'<6 hrs?'/'<7 hrs?' respectively, which implies that postive test results in these tests have a high probability of being true and can therefore be considered in the clinical decision making. The negative predictive values are generally low with exception for test '<7 hrs?'.

Our results indicate that by using repeated timed blood samples and measurement of myoglobin, CK-MB and troponin-T during the first hours alter admission it is possible for the computer method not only to reliably diagnose AMI, but also to predict infarct size and estimate the time after "onset of infarction". This combined approach is of particular clinical relevance:

> The importance of early detection of AMI is emphasized by the reported impressive results of reperfusion by thrombolysis or PTCA on reducing morbidity and mortality (reported by the ISIS-2 (Second International Study of Infarct Survival) Collaborative Group in Lancet 1988;1:349-360; and Grines et al. in N Engl J Med 1993;328(10):673-679).
>
> The importance of adequate timing of the infarct is emphasized by the critical role of time from symptom onset to reperfusion on the effects of the treatment, as reported by the Fibrinolytic Therapy Trialists' (FTT) Collaborative Group in Lancet 1994;343(8893):311–322.

The importance of infarct size prediction is emphasized by the fact the potential benefit of thrombolytic treatment is, while the risk of thrombolysis is not, related to the infarct size, as reported by Mauri et al. in Am J Cardiol 1989;63:1291–1295.

Some patients have difficulties in stating the time of onset of chest pain, and the time from onset of chest pain might be an uncertain estimate for onset of infarction in the individual patient. Therefore, a "second opinion" from the computer, based on the pattern of the biochemical markers, although crude, might be of value for the decision to give or not to give the patient thrombolysis. Although thrombolytic treatment is only proven to be beneficial for patients with ST-elevation or bundle branch block in the ECG on admission it might well be of benefit in certain subgroups of patients with non-diagnostic ECGs, e.g. patients with short delay and an impending large infarction. Given the possibility to select such subgroups, e.g. with the use of neural network methodology, it will be an important area of research to elucidate the value of thrombolysis in these subgroups.

There were no large differences between the computer method and the clinicians in the ability to make a correct diagnosis (except for MMD). However, there seemed to be important differences in the time required to establish the diagnosis. The mean time was shorter and the variation smaller for the computer. If the diagnosis and the infarct size prediction should be of any value for the decision how to treat the patient it must be performed rapidly. The variation in the time needed for the diagnosis and infarct prediction was very small indeed for the computer, while the variation for the clinicians was large, due to both inter-patient and inter-clinician variation. Thus, another possible advantage of the computer method is to provide decision support in order to minimize the effect of the differences in individual clinical knowledge and experience.

The embodiments described above are merely given as examples, and it should be understood that the present invention is not limited thereto. It is of course possible to embody the invention in specific forms other than those described without departing from the spirit of the invention. Further modifications and improvements which retain the basic underlying principles disclosed and claimed herein are within the scope of the present invention.

TABLE 5

Time delay for correct diagnosis

| Test for | Computer method | | Clinicians' assessment | |
|---|---|---|---|---|
| | Number of measurements | Time delay | Number of measurements | Time delay |
| AMI | 1.2 [1, 2] | 6 min [0, 30] | 1.7 [1, 5] | 20 min [0, 120] |
| Non-AMI with MMD | 7.0 [7, 7] | 180 min [180, 180] | 8.3 [2, 11] | 573 min [30, 1080] |
| Non-AMI without MMD | 7.0 [7, 7] | 180 min [180, 180] | 4.7 [1, 10] | 130 min [0, 540] |

The mean time delay (expressed as number of measurements and minutes since the start of measurement) until a correct assessment of AMI, Non-AMI with MMD and Non-AMI without MMD can be done. Turnaround time for laboratory analysis is not included. The range is given in brackets.

TABLE 6

Statistic measures of diagnostic performance

| Test for | Measures of diagnostic performance | Computer method | Clinicians' assessment |
|---|---|---|---|
| AMI | sensitivity | 1.00 [11/11] | 1.00 [11/11, 11/11] |
| | specificity | 0.93 [25/27] | 0.95 [25/27, 26/27] |
| | pos. predictive value | 0.85 | 0.90 [0.85, 0.92] |
| | neg. predictive value | 1.00 | 1.00 [1.00, 1.00] |
| Non-AMI with MMD | sensitivity | 0.62 [5/8] | 0.34 [2/8, 3/8] |
| | specificity | 1.00 [30/30] | 0.98 [29/30, 30/30] |
| | pos. predictive value | 1.00 | 0.83 [0.75, 1.00] |
| | neg. predictive value | 0.91 | 0.84 [0.83, 0.85] |
| Non-AMI without MMD | sensitivity | 1.00 [19/19] | 0.97 [18/19, 19/19] |
| | specificity | 0.95 [18/19] | 0.79 [14/19, 16/19] |
| | pos. predictive value | 0.95 | 0.82 [0.79, 0.86] |
| | neg. predictive value | 1.00 | 0.96 [0.94, 1.00] |

Diagnostic sensitivity, specificity and positive and negative predictive values for the computer method and the assessment by clinicians, for correct assessment of patients with AMI, Non-AMI with MMD or Non-AMI without MMD. Results are expressed as average and range (given in brackets).

TABLE 7

Time delay for prediction of infarct size

| Test for | Computer method | | Clinicians' prediction | |
|---|---|---|---|---|
| | Number of measurements | Time delay | Number of measurements | Time delay |
| Major AMI | 2.0 [1, 3] | 30 min [0, 60] | 4.3 [1, 9] | 119 min [0, 360] |
| Minor AMI | 2.2 [2, 3] | 38 min [30, 60] | 5.9 [2, 12] | 260 min [30, 1080] |

The mean time delay, expressed in number of measurements and minutes since the start of measurement, until a correct prediction of infarct size (major AMI or minor AMI) was achieved. Turnaround time for laboratory analysis is not included.

TABLE 8

Statistic measures of diagnostic performance of infarct size prediction

| Measures of diagnostic performance | Computer method | Clinician (Average) [Range] |
|---|---|---|
| sensitivity | 1.00 [6/6] | 0.83 [4/6, 6/6] |
| specificity | 0.80 [4/5] | 0.93 [4/5, 5/5] |
| pos. predictive value | 0.86 | 0.95 [0.86, 1.00] |
| neg. predictive value | 1.00 | 0.85 [0.71, 1.00] |

Diagnostic sensitivity, specificity and positive and negative predictive values for infarct size prediction by the computer method and the prediction of clinicians, major AMI = positive test result, minor AMI = negative test result. The range is given in brackets.

TABLE 9

Statistic measures of diagnostic performance of assessment of 'time from onset'

| Measures of diagnostic performance | ≦5 hrs? | ≦6 hrs? | ≦7 hrs? |
|---|---|---|---|
| sensitivity | 0.50 | 0.83 | 1.00 |
|  | (16/32) | (39/47) | (59/59) |
| specificity | 0.91 | 0.47 | 0.39 |
|  | (41/45) | (14/30) | (7/18) |
| pos predictive value* | 0.93 | 0.79 | 0.79 |
| neg predictive value* | 0.44 | 0.54 | 1.00 |

Diagnostic sensitivity, specificity and positive and negative predictive values of the computer method for correct assessment of patients with AMI having a time from onset of infarction less than (positive test result)/greater then (negative test result) 5, 6, 7 hours resp.
*)Predictive values are calculated according to prevalences from the UUH/CCU 1994 material.

APPENDIX

P12–P15, eq. 7a (4 Single Layer Perceptrons with 3 input units and 1 output unit)
$w_{ik}$ (i = 1, 4; k = 1, 3)
30.0105  90.4493  −32.1904
108.8995  297.5194  −118.7127
34.6056  114.0029  −30.4831
6.1632  19.6807  −3.7886
$b_i^T$ (i = 1, 4)
−22.8082 −77.4259 −42.7468 −12.6341
P22, eq. 9a (Elman Network with 3 input units, 10 feedback units and 1 output unit)
$w_{ik}$ (i = 1, 10; k = 1, 13)
0.2775 −0.4976 0.3415 −1.0535 1.9259 −0.2033 0.2008 −0.4487
−0.4947 −0.0797 −1.4021 0.2266 0.6740
−0.7723 1.2197 0.0263 −0.0574 0.0203 −0.2849 0.6930 0.2237
0.1590 0.4548 −0.4271 −0.2682 −0.0406
−0.5913 0.4647 0.4536 0.2256 0.1712 0.1385 −0.1948 −0.3311
0.0785 −0.4588 −0.2606 0.2203 −0.0737
−0.1118 −0.2173 −0.2022 0.1967 0.0643 0.2299 −0.2719 0.3194
0.0100 0.1623 0.2263 −0.3923 0.0820
0.1673 −0.1331 0.1081 −0.3037 −0.0933 0.5738 0.2752 0.3794
0.0962 −0.1584 −0.1852 −0.0342 0.2423
0.1920 −0.3557 −0.1747 0.4023 0.4246 −0.7841 0.1556 −0.2522
−0.1607 0.5301 0.1441 −0.0444 0.2255
−0.0183 −0.3364 −0.0322 0.1764 0.0208 0.1454 −0.0116 0.1576
−0.1006 −0.0345 −0.1388 −0.1439 −0.2101
0.1482 0.0488 0.4417 0.2143 0.3588 −0.1948 −0.2588 0.2558
0.0218 0.1234 −0.4755 −0.0722 0.1526
0.1002 0.1995 −0.3192 0.5329 0.0420 0.2765 −0.0363 0.3273
−0.4432 0.3296 −0.0346 −0.0874 0.4017
−0.1140 −0.3255 −0.0067 −0.2191 −0.2389 0.2739 −0.4633 0.2672
0.1346 0.0927 0.0141 −0.2041 0.1848
$b_i^T$ (i = 1, 10)
−0.3238 0.5222 −0.0316 1.3180 −0.6551 −0.7831 −0.6776 0.9335
−0.7658 0.2893
P22, eq. 9d
$w_1$ (i = 1, 10)
0.9285 0.4873 0.6946 −0.0688 0.9849 0.3939 0.3444 −0.4073
−0.0745 0.4423
b
0.8919
P32, eq. 11a (Single Layer Perceptron with 6 input units and 1 output unit)
$w_k$ (k = 1, 6)
6.3370  7.0658  4.0925  1.8062  0.3001  1.4579
b
−33.9156
P43, eq. 17a (Single Layer Perceptron with 2 input units and 3 output units)
$w_{ik}$ (i = 1, 3; k = 1, 2)
1.7985 −26.9445
0.2009 −9.6437
11.4465 −10.4472
$b_i^T$ (i = 1, 3)
0.9275 1.3129 0.0489

APPENDIX-continued

P52, eq. 9a (Elman Network with 3 input units, 10 feedback units and 1 output unit)
$w_{ik}$ (i = 1, 10; k = 1, 13)
−0.3389 −0.3367 0.5286 1.5057 0.1340 −0.2581 −0.7473 0.6101
−0.6717 −1.1043 2.1864 −1.2987 −0.8498
−0.0525 −1.2433 1.5282 −0.9381 −0.6002 −0.8809 0.3922 2.0293
0.4936 −0.7383 0.5411 −0.6927 0.0451
1.4807 −0.3885 −0.3900 −0.7625 −0.4389 0.3026 0.0502 0.0140
−0.2277 1.0623 0.5152 0.3624 −0.2727
0.0380 −0.1836 −0.6187 0.3080 0.4949 0.2324 0.3405 0.3569
−0.6686 −0.0560 −0.2155 0.2240 0.0055
0.2977 −0.5306 0.3065 −0.0069 −0.7437 0.1863 −0.0929 −0.4340
−0.3432 0.0955 −0.3925 0.0201 0.3096
0.4922 0.0315 0.0550 0.4416 0.2677 0.2594 −0.1170 −0.5704
−0.2494 −0.1857 −0.5513 −0.6876 0.4356
0.4952 −0.5706 0.8645 −0.1603 0.1222 0.3438 −0.5513 0.7544
0.6457 0.7878 −0.1392 1.2805 −0.3421
−0.0717 0.3055 −0.0067 −0.1094 −0.3521 0.4419 −0.0223 −0.4482
−0.2350 0.4473 0.2304 0.0669 0.3961
0.2324 −0.7408 −0.6664 −0.1821 0.0698 0.0092 0.4263 −0.3199
0.6471 0.1921 −0.2497 −0.5118 −0.1825
−0.4539 −0.4616 0.1438 0.2697 −0.2158 0.1982 0.3357 −0.3519
−0.9251 −0.2619 −0.1242 0.0463 −0.2608
$b_i^T$ (i = 1, 10)
−0.2094 −0.0973 −0.1705 −0.5900 0.2288 −0.0337 −0.0895 0.8852
0.3331 0.6697
P52, eq. 9d
$w_i$ (i = 1, 10)
1.2067 0.0922 0.9421 −0.0245 −0.3283 1.3672 −0.7359 0.0195
−0.1615 −1.0108
b
0.4467

We claim:

1. A method for early detection of acute myocardial infarction (AMI) in a patient, comprising the steps of:
   measuring, with a predetermined timing and at at least two different time instances occurring within 3 hours from admission of said patient, concentration levels of at least two biochemical markers of AMI in plasma of said patient, said at least two biochemical markers having different rates of appearance in said plasma at AMI;
   generating an indication of AMI based on a first predetermined set of said concentration levels and first empirical data comprising concentration levels obtained from previous patients with AMI/non-AMI and a preclassification of the presence/absence of AMI in said previous patients by using a neural network structure trained with said first empirical data to detect marker-patterns of AMI; and
   predicting the infarct size based on a second predetermined set of said concentration levels and second empirical data comprising concentration levels obtained from previous patients with different infarct sizes and a preclassification of the infarct sizes of said previous patients, whereby an early detection of AMI and an early infarct size prediction are obtained.

2. A method according to claim 1, wherein said first predetermined set comprises concentration levels measured at at least one of said at least two time instances, and said second predetermined set comprises concentration levels measured at more than one of said at least two time instances.

3. A method according to claim 1, wherein said at least two biochemical markers are selected from the following group consisting of: myoglobin, creatine kinase MB, troponin-T, troponin-I, glycogen phosphorylase BB, lactate dehydrogenase, and heart-type fatty acid binding protein (h-FABP).

4. A method according to claim 1, wherein said predetermined timing generally corresponds to the timing with which the concentration levels of said first and second empirical data were obtained.

5. A method according to claim 1, wherein said neural network structure comprises at least two neural networks, each one of which is trained to detect AMI within an individual defined period of time after onset of symptoms of infarction for generating an individual indication of AMI/non-diagnosis, said individual indications being used for generating said indication of AMI.

6. A method according to claim 1, wherein said neural network structure comprises a feedback connection for recognizing temporal patterns of the concentration levels of said first predetermined set, said first predetermined set comprising concentration levels measured at more than one of said at least two time instances.

7. A method according to claim 1, wherein said predicting step comprises the step of using a further neural network structure trained with said second empirical data to detect marker-patterns of different infarct sizes.

8. A method according to claim 1 further comprising the step of generating, based on a third predetermined set of said concentration levels and third empirical data comprising concentration levels obtained from previous patients of different states regarding the time after onset of infarction and a preclassification of the times after onset for said previous patients, at least one time estimate representing a time period within which onset of infarction occurred.

9. A method according to claim 8, wherein said step of generating at least one time estimate comprises the step of using a third neural network structure trained with said third empirical data to detect marker-patterns of times after onset of infarction.

10. A method according to claim 9, wherein at least two time estimates are generated, said method further comprising the step of sending said at least two time estimates to a decision table for generating a final estimate of a time period within which said onset of infarction occurred.

11. A method according to claim 1, wherein said step of generating an indication of AMI further comprises the step of preprocessing said concentration levels, and wherein said preprocessed concentration levels are processed by said neural network structure.

12. An apparatus for early detection of acute myocardial infarction (AMI) in a patient, comprising:

means for performing timed measurements, at at least two different time instances occurring within 3 hours from admission of said patient, of concentration levels of at least two biochemical markers of AMI in plasma of said patient, said at least two biochemical markers having different rates of appearance in said plasma at AMI;

a neural network structure for generating an indication of AMI based on a first predetermined set of said concentration levels and first empirical data comprising concentration levels obtained from previous patients with AMI/non-AMI and a preclassification of the presence/absence of AMI in said previous patients, said neural network structure being trained with said first empirical data to detect marker-patterns of AMI; and means for predicting the infarct size based on a second predetermined set of said concentration levels and second empirical data comprising concentration levels obtained from previous patients with different infarct sizes and a preclassification of the infarct sizes of said previous patients.

13. An apparatus according to claim 12, wherein said neural network structure comprises at least two neural networks, each one of which is associated with a separate period of time after onset of symptoms of infarction for generating an individual indication of AMI/non-diagnosis; and wherein said apparatus further comprises means for generating said indication of AMI based on said individual indications of AMI/non-diagnosis.

14. An apparatus according to claim 12, wherein said neural network structure is a two-layer neural network with a feedback connection for recognizing temporal patterns of the concentration levels of said first predetermined set so as to generate said indication of AMI.

15. An apparatus according to claim 12, wherein said predicting means comprises a further neural network structure trained with said second empirical data to detect marker-patterns of different infarct sizes.

16. An apparatus according to claim 12 further comprising means for generating, based on a third predetermined set of said concentration levels and third empirical data comprising concentration levels obtained from previous patients of different states regarding the time after onset of infarction and a preclassification of the times after onset for said previous patients, at least one time estimate representing a time period within which onset of infarction occurred.

17. An apparatus according to claim 16, wherein said means for generating at least one time estimate comprises a neural network structure trained with said third empirical data to detect marker-patterns of times after onset of infarction.

18. An apparatus according to claim 12 further comprising a unit for preprocessing said concentration levels, and wherein said preprocessed concentration levels are processed by said neural network structure.

19. A method for early detection of acute myocardial infarction (AMI) in a patient, comprising the steps of:

performing timed measurements, at at least two different time instances occurring within 3 hours from admission of said patient, of concentration levels of at least two biochemical markers of AMI in plasma of said patient, said at least two biochemical markers having different rates of appearance in said plasma at AMI;

generating an indication of AMI based on a first predetermined set of said concentration levels and first empirical data comprising concentration levels obtained from previous patients with AMI/non-AMI and a preclassification of the presence/absence of AMI in said previous patients by using a neural network structure trained with said first empirical data to detect marker-patterns of AMI;

predicting the infarct size based on a second predetermined set of said concentration levels and second empirical data comprising concentration levels obtained from previous patients with different infarct sizes and a preclassification of the infarct sizes of said previous patients; and generating, based on a third predetermined set of said concentration levels and third empirical data comprising concentration levels obtained from previous patients of different states regarding the time after onset of infarction and a preclassification of the times after onset for said previous patients, at least one time estimate representing a time period within which onset of infarction occurred, whereby an early detection of AMI, an early infarct size prediction and an early estimate of the time after onset of AMI are obtained.

20. A method for:
a) early detection/exclusion of acute myocardial infarction (AMI) in a patient;
b) predicting the infarct size;
c) estimating the time after onset of infarction;
d) assessing/excluding possible minor myocardial damage (MMD), said method comprising the steps of:
  measuring, with a predetermined timing and at at least two different time instances occurring within 3 hours from admission of said patient, concentration levels of at least two biochemical markers of AMI in plasma of said patient, said at least two biochemical markers having different rates of appearance in said plasma at AMI;
  generating an indication of AMI/non-diagnosis by making a comparison based on a first predetermined set of said concentration levels and first empirical data comprising concentration levels obtained from previous patients with AMI/non-AMI and a preclassification of the presence/absence of AMI in said previous patients by using a neural network structure trained with said first empirical data to detect marker-patterns of AMI;
  predicting the infarct size by making a comparison based on a second predetermined set of said concentration levels andsecond empirical data comprising concentration levels obtained from previous patients with different infarct sizes and a preclassification of the infarct sizes of said previous patients, provided an indication of AMI has been generated;
  generating, by making a comparison based on a third predetermined set of said concentration levels and third empirical data comprising concentration levels obtained from previous patients of different states regarding the time after onset of infarction and a preclassification of the times after onset for said previous patients, an estimate representing a time period within which onset of infarction occurred, provided an indication of AM/has been generated;
  excluding AMI provided said indication of AMI has not been generated for a predetermined period of time; and
  assessing/excluding MMD by making a comparison based on a fourth predetermined set of said concentration levels and fourth empirical data comprising concentration levels obtained from previous patients with MMD/without MMD and a preclassification of the presence/absence of MMD in said previous patients, provided AMI has been excluded.

21. A method for early detection of acute myocardial infarction (AMI) in a patient, comprising the steps of:
  measuring, with a predetermined timing and at at least two different time instances occurring within 3 hours from admission of said patient, concentration levels of least two biochemical markers of AMI in plasma of said patient, said at least two biochemical markers having different rates of appearance in said plasma at AMI;
  generating an indication of AMI based on a first predetermined set of said concentration levels and first empirical data comprising concentration levels obtained from previous patients with AMI/non-AMI and a preclassification of the presence/absence of AMI in said previous patients by using a neural network structure trained with said first empirical data to detect marker-patterns of AMI; and
  generating, based on a third predetermined set of said concentration levels and third empirical data comprising concentration levels obtained from previous patients of different states regarding the time after onset of infarction and a preclassification of the times after onset for said previous patients, an estimate of a time period within which onset of infarction occurred,
  whereby an early detection of AMI and an early estimate of the time after onset of AMI are obtained.

22. An apparatus for excluding acute myocardial infarction (AMI) in a patient, comprising:
  means for measuring, with a predetermined timing and within 3 hours from admission of said patient, concentration levels of at least two biochemical markers of AMI in plasma of said patient, said at least two biochemical markers having different rates of appearance in said plasma at AMI;
  means for generating an indication of AMI based on a first predetermined set of said concentration levels and first empirical data comprising concentration levels obtained from previous patients with AMI/non-AMI and a preclassification of the presence/absence of AMI in said previous patients by using a neural network structure trained with said first empirical data to detect marker-patterns of AMI; and
  means for excluding AMI as a diagnosis provided said indication of AMI has not been generated for a predetermined period of time.

23. Apparatus according to claim 22 further comprising means for assessing/excluding minor myocardial damage (MMD) based on said concentration levels and fourth empirical data comprising concentration levels obtained from previous patients with MMD/without MMD and a preclassification of the presence/absence of MMD in said previous patients, provided AMI has been excluded as a diagnosis.

24. An apparatus according to claim 23, wherein said means for assessing/excluding MMD comprises a fourth neural network structure trained with said fourth empirical data to detect marker-patterns of MMD, said neural network structure comprising a feedback connection for recognizing temporal patterns of said concentration levels.

25. A method for excluding acute myocardial infarction (AMI) as a diagnosis for a patient, comprising the steps of:
  performing timed measurements, at at least two different time instances occurring within 3 hours from admission of said patient, of concentration levels of at least two biochemical markers of AMI in plasma of said patient, said at least two biochemical markers having different rates of appearance in said plasma at AMI;
  generating an indication of non-diagnosis based on a first predetermined set of said concentration levels and first empirical data comprising concentration levels obtained from previous patients with AMI/non-AMI and a preclassification of the presence/absence of AMI in said patients, by using a neural network structure trained with said first empirical data to detect marker-patterns of AMI;
  excluding AMI as a diagnosis provided said indication of non-diagnosis has been generated for a predetermined period of time; and
  assessing/excluding minor myocardial damage (MMD) based on said concentration levels and fourth empirical data comprising concentration levels obtained from previous patients with MMD/without MMD and a preclassification of the presence/absence of MMD in said previous patients, provided AM/has been excluded as a diagnosis,
  whereby an early exclusion of AMI and an assessment/exclusion of MMD are obtained.

26. A method according to claim 25, wherein said step of assessing/excluding MMD comprises the step of using a neural network structure trained with said fourth empirical data to detect marker-patterns of MMD.

27. A method according to claim 26, wherein said neural network structure comprises a feedback connection for recognizing temporal patterns of said concentration levels.

28. An apparatus for early detection of acute myocardial infarction (AMI) in a patient, comprising:

means for measuring concentration levels of at least two biochemical markers of AMI in plasma of said patient and for generating signals representing said concentration levels, said at least two biochemical markers having different rates of appearance in said plasma at AMI;

a neural network structure responsive to said signals and trained with empirical data comprising concentration levels obtained from previous patients with AMI/non-AMI and a preclassification of the presence/absence of AMI in said previous patients to detect marker-patterns of AMI, said neural network structure comprising at least two neural networks, each one of which is trained to detect AMI within an individual defined time period after onset of symptoms of infarction for generating an individual indication of AMI/non-diagnosis; and means for generating a conclusive indication of AMI based on said individual indications.

29. An apparatus according to claim 28, further comprising means for generating an estimate representing a time period within which onset of infarction occurred based on said individual defined time periods and said individual indications.

30. An apparatus for early detection of acute myocardial infarction (AMI) in a patient, comprising:

means for measuring concentration levels of at least two biochemical markers of AMI in plasma of said patient and for generating signals representing said concentration levels, said at least two biochemical markers having different rates of appearance in said plasma at AMI;

a neural network structure responsive to said signals and trained with empirical data comprising concentration levels obtained from previous patients with AMI/non-AMI and a preclassification of the presence/absence of AMI in said previous patients to detect marker-patterns of AMI, said neural network structure comprising a feedback connection for recognizing temporal patterns of said concentration levels so as to generate an indication of AMI.

31. An apparatus for early detection of acute myocardial infarction (AMI) in a patient, comprising:

means for measuring concentration levels of at least two biochemical markers of AMI in plasma of said patient and for generating signals representing said concentration levels, said at least two biochemical markers having different rates of appearance in said plasma at AMI;

a first neural network structure responsive to the initial signals and trained with first empirical data comprising concentration levels obtained from previous patients with AMI/non-AMI and a preclassification of the presence/absence of AMI in said previous patients to detect marker-patterns of AMI, said first neural network structure comprising at least two neural networks, each one of which is associated with a separate period of time after onset of symptoms of infarction for generating an individual indication of AMI/non-diagnosis;

means for generating a first indication of AMI/non-diagnosis based on said individual indications; and a second neural network structure responsive to said signals and trained with said first empirical data to detect marker-patterns of AMI, said second neural network structure comprising a feedback connection for recognizing temporal patterns of said concentration levels so as to generate a second indication of AMI provided said first indication of AMI was not generated.

32. A method for early detection of acute myocardial infarction (AMI) in a patient, comprising the steps of:

measuring concentration levels of at least two biochemical markers of AMI in plasma of said patient, said at least two biochemical markers having different rates of appearance in said plasma at AMI;

generating an indication of AMI based on a first predetermined set of said concentration levels and empirical data comprising concentration levels obtained from previous patients with AMI/non-AMI and a preclassification of the presence/absence of AMI in said previous by using a neural network trained with said first empirical data to detect marker-patterns of AMI, the training of said neural network being performed by maximizing the net gain of weighted true and false classifications.

33. A method for predicting infarct size for a patient with acute myocardial infarction (AMI), comprising the steps of:

measuring concentration levels of at least two biochemical markers of AMI in plasma of said patient, said at least two biochemical markers having different rates of appearance in said plasma at AMI; and predicting the infarct size based on said concentration levels and empirical data comprising concentration levels obtained from previous patients with different infarct sizes and a preclassification of the infarct sizes of said previous patients by using a neural network trained with said empirical data to detect marker-patterns of different infarct sizes.

34. A method for assessing minor myocardial damage (MMD) in a patient, comprising the steps of:

measuring concentration levels of at least two biochemical markers of AMI in plasma of said patient, said at least two biochemical markers having different rates of appearance in said plasma at AMI; and assessing/excluding MMD based on said concentration levels and empirical data comprising concentration levels obtained from previous patients with MMD/without MMD and a preclassification of the presence/absence of MMD in said previous patients by using a neural network structure trained with said empirical data to detect marker-patterns of MMD.

35. A method for estimating the time after onset of infarction in a patient with acute myocardial infarction, comprising the steps of:

measuring concentration levels of at least two biochemical markers of AMI in plasma of said patient, said at least two biochemical markers having different rates of appearance in said plasma at AMI; and generating an estimate representing a time period within which onset of infarction occurred by making a comparison based on said concentration levels and empirical data comprising concentration levels obtained from previous patients of different states regarding the time after onset of infarction and a preclassification of the times after onset of infarction for said previous patients.

* * * * *